United States Patent [19]
Fields

[11] Patent Number: 5,726,243
[45] Date of Patent: Mar. 10, 1998

[54] MILD SOLID-PHASE SYNTHESIS OF ALIGNED, BRANCHED TRIPLE-HELICAL PEPTIDES

[75] Inventor: Gregg B. Fields, Brooklyn Park, Minn.

[73] Assignee: Regents of the University of Minnesota, Minneapolis, Minn.

[21] Appl. No.: 675,140

[22] Filed: Jul. 3, 1996

Related U.S. Application Data

[62] Division of Ser. No. 534,342, Sep. 27, 1995, Pat. No. 5,576,419, which is a continuation of Ser. No. 85,633, Jun. 30, 1993, abandoned.

[51] Int. Cl.$^6$ .................. C07K 1/04; C07K 1/06; C07K 14/78; C08G 69/10
[52] U.S. Cl. ............ 525/54.11; 530/334; 530/336; 530/337; 530/356; 530/810; 530/812; 530/816
[58] Field of Search ................ 525/54.1, 54.11; 530/810, 811, 812, 815, 816, 356, 334, 336, 337

[56] References Cited

U.S. PATENT DOCUMENTS

| | | | |
|---|---|---|---|
| 4,062,746 | 12/1977 | Rich et al. | 530/334 |
| 4,108,846 | 8/1978 | Meienhofer | 530/334 |
| 5,576,419 | 11/1996 | Fields | 530/322 |

OTHER PUBLICATIONS

J.G. Adamson et al., "Use of Marfey's Reagent to Quantitate Racemization upon Anchoring of Amino Acids to Solid Supports for Peptide Synthesis," *Anal. Biochem.*, 202, 210–214 (1992).

Albericio et al., "Allyl–based orthogonal solid phase Peptide synthesis," *Peptides 1992 (Proceedings of the Twenty–Second European Peptide Symposium, Sep. 13–19, 1992, Interlaken, Switzerland)*, ESCOM, Leiden, pp. 191–193 (1993).

G. Barany et al., "A New Amino Protecting Group Removable by Reduction. Chemistry of the Dithiasuccinoyl (Dts) Function," *J. Am. Chem. Soc.*, 99, 7363–7365 (1977).

K. Barlos et al., "Application of the Trt and Fmoc Groups for the Protection of Polyfunctional α–Amino Acids," *Liebigs. Ann. Chem.*, 1025–1030 (1987).

B. Brodsky et al., "NMR and CD Studies of Triple–Helical Peptides," *Biopolymers*, 32, 447–451 (1992).

B.W. Bycroft et al., "A Novel Lysine–protecting Procedure for Continuous Flow Solid Phase Synthesis of Branched Peptides," *J. Chem. Soc., Chem. Commun.*, 778–779 (1993).

M.K. Chelberg et al., "Type IV Collagen–mediated Melanoma Cell Adhesion and Migration: Involvement of Multiple, Distinct Domains of the Collagen Molecule," *Cancer Research*, 49, 4796–4802 (1989).

(List continued on next page.)

*Primary Examiner*—Jeffrey E. Russel
*Attorney, Agent, or Firm*—Mueting, Raasch, Gebhardt & Schwappach, P.A.

[57] ABSTRACT

A triple-helical polypeptide of the formula:

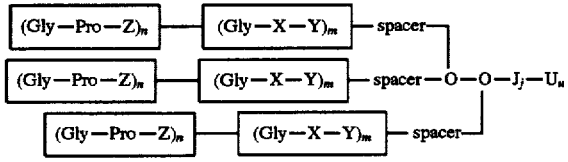

is provided wherein: Z is Hyp or Pro; each X and Y is an amino acid such that $(Gly\text{-}X\text{-}Y)_m$ is a sequence of a collagen cell adhesion site; said X and Y may be the same or different and each (Gly-X-Y) may be the same or different; O is an amino acid having a single side-chain amino group; J is an amino acid capable of acting as a chromophore; U is an amino acid; $u=0$ or 1; $n \leq 30$; $m \leq 30$; $m+n \leq 30$; and $j \geq 1$. Methods of making these compounds and intermediates used in the methods, are also provided.

11 Claims, 8 Drawing Sheets

OTHER PUBLICATIONS

M.K. Chelberg et al., "Characterization of a Synthetic Peptide from Type IV Collagen That Promotes Melanoma Cell Adhesion, Spreading, and Motility," *J. Cell. Biol.*, 111, 261–270 (1990).

O. Dangles et al., "Selective Cleavage of the Allyl and Allyloxycarbonyl Groups through Palladium–Catalyzed Hydrostannolysis with Tributyltin Hydride. Application to the Selective Protection–Deprotection of Amino Acid Derivatives and in Peptide Synthesis," *J. Org. Chem.*, 52, 4984–4993 (1987).

B.B. Doyle et al., "Collagen Polymorphism: Its Origins in the Amino Acid Sequence," *J. Mol. Biol.*, 91, 79–99 (1975).

J. Engel et al., "The Triple Helix=Coil Conversion of Collagen–Like Polytripeptides in Aqueous and Nonaqueous Solvents. Comparison of the Thermodynamic Parameters and the Binding of Water to (L–Pro–L–Pro–Gly)$_n$ and (L–Pro–L–Hyp–Gly)$_n$," *Biopolymers*, 16, 601–622 (1977).

C.G. Fields et al., "Solid phase peptide synthesis of $^{15}$N–gramicidins A, B, and C and high performance liquid chromatographic purification," *Int. J. Peptide Protein Res.*, 33, 298–303 (1989).

C.G. Fields et al., "Three–dimensional orthogonal solid–phase synthesis of cell–adhesive, triple–helical collagen–model peptides," *Peptide Chemistry 1992 (Proceedings of the 2nd Japan Symposium on Peptide Chemistry, Nov. 9–13, 1992, Shizuoka, Japan)*, ESCOM, Leiden, pp. 14–18 (1993).

C.G. Fields et al., "The Development of High–Performance Liquid Chromatographic Analysis of Allyl and Allyloxycarbonyl Side–Chain–Protected Phenylthiohydantoin Amion Acids," *Anal. Biochem.*, 203, 245–251 (1992).

C.G. Fields et al., "HBTU Activation for Automated Fmoc Solid–Phase Peptide Synthesis," *Peptide Research*, 4, 95–101 (1993).

C.G. Fields et al., "Edman Degradation Sequence Analysis of Resin–Bound Peptides Synthesized by 9–Fluorenylmethoxycarbonyl Chemistry," *Peptide Research*, 6, 39–47 (1993).

G.B. Fields et al., "Solid Phase Peptide Synthesis Utilizing 9–Fluorenylmethoxycarbonyl Amino Acids," *Int. J. Peptide Protein Res.*, 35, 161–214 (1990).

G.B. Fields et al., "The Versatility of Solid Phase Peptide Synthesis," in *Innovation and Perspectives in Solid Phase Synthesis;* R. Epton, Ed.; Solid Phase Conference Coordination, Ltd.: Birmingham, U.K., pp. 241–260, (1990).

G.B. Fields et al., "Optimization Strategies for FMOC Solid–Phase Peptide Synthesis: Synthesis of Triple–Helical Collagen–Model Peptides," in *Innovation and Perspective in Solid Phase Synthesis–Peptides, Polypeptides and Oligonucleotides*, Abstract No. 118:125044 (1992), R. Epton Ed., Solid Phase Conference Coordination, Ltd.: Birmingham, U.K. (1992).

G.B. Fields et al., "Principles and Practice of Solid–Phase Peptide Synthesis," in *Synthetic Peptides: A User's Guide*, G.A. Grant, Ed., W.H. Freeman & Co., New York, NY; pp. 77–183, (1992).

H.P. Germann et al., "A Synthetic Model of Collagen: An Experimental Investigation of the Triple–Helix Stability," *Biopolymers*, 27, 157–163 (1988).

M.R. Ghadiri et al., "A Convergent Approach to Protein Design. Metal Ion–Assisted Spontaneous Self–Assembly of a Polypeptide into a Triple–Helix Bundle Protein," *J. Am. Chem. Soc.*, 114, 825–831 (1992).

U.B. Goli et al., "Synthetic Triple Helical Models for the Collagen Cleavage Site in Interstitial Collagens", *MATRIX*, 71–72 (1992).

F. Guibé et al., "Use of an Allylic Anchor Group and of its Palladium Catalyzed Hydrostannolytic Cleavage in the Solid Phase Synthesis of Protected Peptide Fragments," *Tetrahedron Letters*, 30, 2641–2644 (1989).

N. Jentoft et al., "Labeling of Proteins by Reductive Methylation Using Sodium Cyanoborhydride," *J. Bio. Chem.*, 254, 4359–4365 (1979).

P. Lloyd–Williams et al., "Solid–Phase Synthesis of Peptides Using Allylic Anchoring Groups. An Investigation of Their Palladium–Catalyzed Cleavage," *Tetrahedron Letters*, 32, 4207–4210 ( 1991 ).

R. Matsueda et al., "3–Nitro–2–Pyridinesulfenyl (Npys) Group. A Novel Selective Protecting Group Which Can Be Activated for Peptide Bond Formation," *Int. J. Peptide Protein Res.*, 16, 392–401 (1980).

D.G. Mullen et al., "A New Fluoridolyzable Anchoring Linkage for Orthogonal Solid–Phase Peptide Synthesis: Design, Preparation, and Application of the N–(3 or 4)–[[4–(Hydroxymethyl)phenoxy]–tert–butylphenylsilyl]phenyl Pentanedioic Acid Monoamide (Pbs) Handle," *J. Org. Chem.*, 53, 5240–5248 (1988).

M. Mutter et al., "A Chemical Approach to Protein Design–Template–Assembled Synthetic Proteins (TASP)," *Angew. Chem. Int. Ed. Engl.*, 28, 535–554 (1989).

B.R. Olsen et al., "The Synthetic Polytripeptides (Pro–Pro–Gly)$_{10}$ and (Pro–Pro–Gly)$_{20}$ Form Micro–crystalline Structures Similar to Segmental Structures formed by Collagen," *J. Mol. Biol.*, 57, 589–595 (1971).

A. Patchornik et al., "Photosensitive Protecting Groups," *J. Am. Chem. Soc.*, 92, 6333–6335 (1970).

W. Roth et al., "Die Struktur kollagenähnlicher Homo– und Heteropolytripeptide, 4$^{a)}$. Polytripeptide durch repetitive Peptidsynthese und Verbrückung von Oligopeptiden," *Makromol. Chem.*, 180, 905–917 (1979).

W. Roth et al., "Triple Helix–Coil Transition of Covalently Bridged Collagenlike Peptides," *Biopolymers*, 19, 1909–1917 (1980).

S. Sakakibara et al., "Synthesis of Poly–(L–prolyl–L–prolylglycyl) of Defined Molecular Weight," *Bull. Chem. Soc. Jpn.*, 41, 1273 (1968).

W.J.G. Schielen et al., "Use of Mpc–amino acids in solid phase peptide synthesis leads to improved coupling efficiencies," *Int. J. Peptide Protein Res.*, 37, 341–346 (1991).

J. Shao et al., "A Test–Case for the 1–(1–Adamantyl)–1–Methylethoxycarbonyl (ADPOC) Group: Solid–Phase Synthesis of LH–RH Using N$^\alpha$–ADPOC Protection and an Acid Labile Handle," *Tetrahedron Letters.*, 32, 345–346 (1991).

K. Sutoh et al., "Conformational Change of the Triple–Helical Structure. I. Synthesis of Model Peptides of Collagen by the Solid–Phase Method," *Biopolymers*, 13, 2385–2390 (1974).

K. Sutoh et al., "Conformational Change of the Triple–Helical Structure. II. Conformation of (Pro–Pro–Gly)$_n$ and (Pro–Pro–Gly)$_n$(Ala–Pro–Gly)$_m$(Pro–Pro–Gly)$_n$ in an Aqueous Solution," *Biopolymers*, 13, 2391–2404 (1974).

J.P. Tam et al., "Strong Acid Deprotection of Synthetic Peptides: Mechanisms and Methods," in *The Peptides*, vol. 9, Academic Press, Inc.; pp. 185–248, (1967).

S. Thakur et al., "Influence of Different Tripeptides on the Stability of the Collagen Triple Helix. II. An Experimental Approach with Appropriate Variations of a Trimer Model Oligotripepetide," *Biopolymers*, 25, 1081–1086 (1986).

P. Vandenberg et al., "Characterization of a Type IV Collagen Major Cell Binding Site with Affinity to the α1β1 and the α2β1 Integrins," *J. Cell. Biol.*, 113, 1475–1483 (1991).

C. Voss et al., "Synthetic Insuline by Seletive Disulfide Bridging. II. Polymer Phase Synthesis of the Human B Chain Fragments," *Hoppe–Seyler's Z. Physiol. Chem.*, 362, 717–725 (Jun. 1981).

J.D. Wade et al., "DBU as an $N^\alpha$–Deprotecting Reagent for the Fluorenyl–methoxycarbonyl Group in Continuous Flow Solid–Phase Peptide Synthesis," *Peptide Res.*, 4, 194–199 (1991).

S.S. Wang et al., "Preparation of Some New Biphenylisopropyloxycarbonyl Amino Acids and Their Application to the Solid Phase Synthesis of a Tryptophan–Containing Heptapeptide of Bovine Parathyroid Hormone," *Int. J. Protein Research I.*, 235–244 (1969).

S.S. Wang et al., "Solid Phase Synthesis of Protected Peptides via Photolytic Cleavage of the α–Methylphenacyl Ester Anchoring Linkage," *J. Org. Chem.*, 41, 3258–3261 (1976).

S.S. Wang et al., "4–Methoxybenzyloxycarbonyl Amino Acids in Solid Phase Peptide Synthesis," *Int. J. Peptide Protein Res.*, 30, 662–667 (1987).

R.W. Weber et al., "The Influence of O–Acetylation upon the Conformational Behaviour of the Collagen Model Peptide (L–Pro–L–Hyp–Gly)$_{10}$ and of Gelatin," *Helvetica Chimica Acta*, 61, 701–708 (1978).

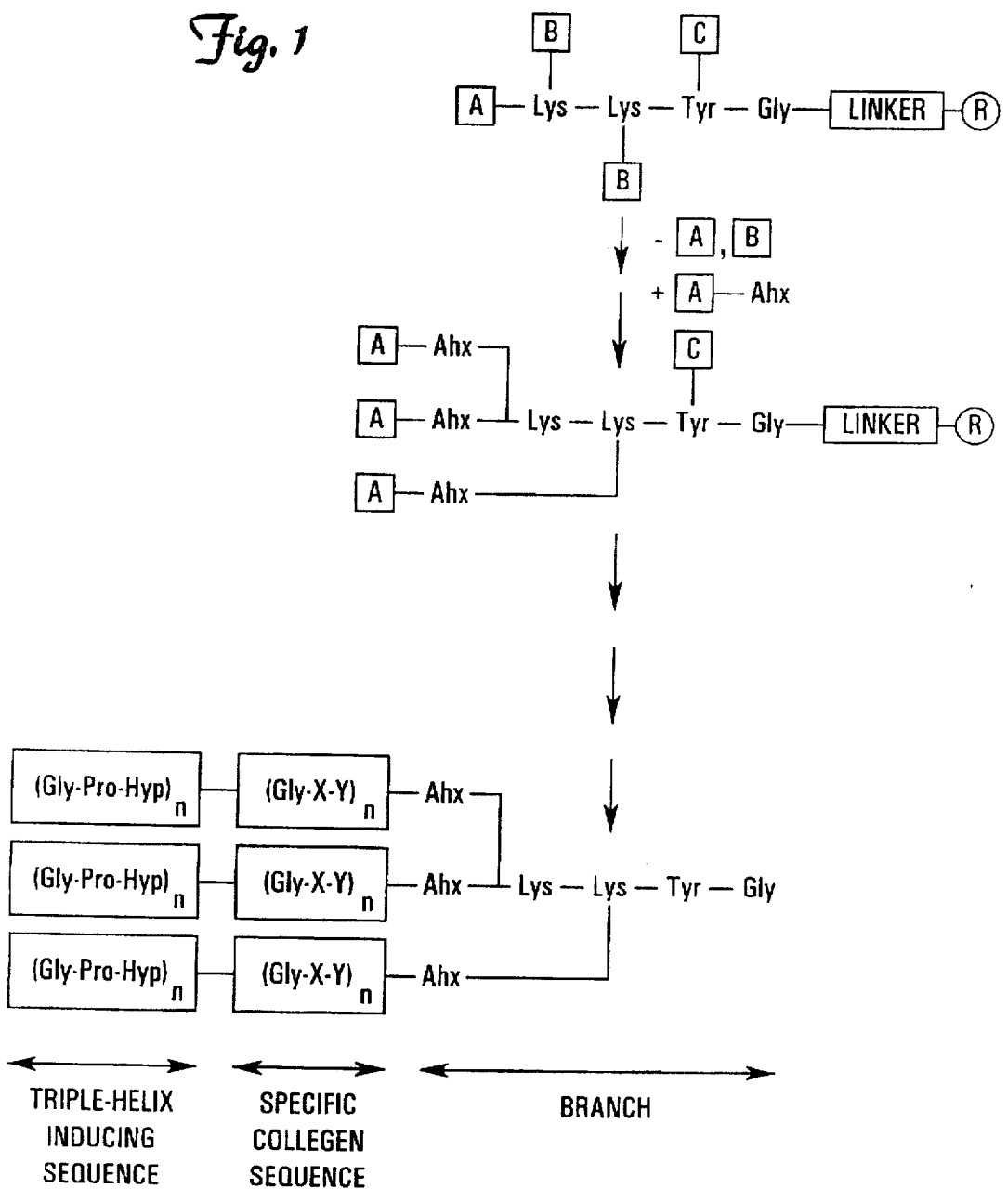

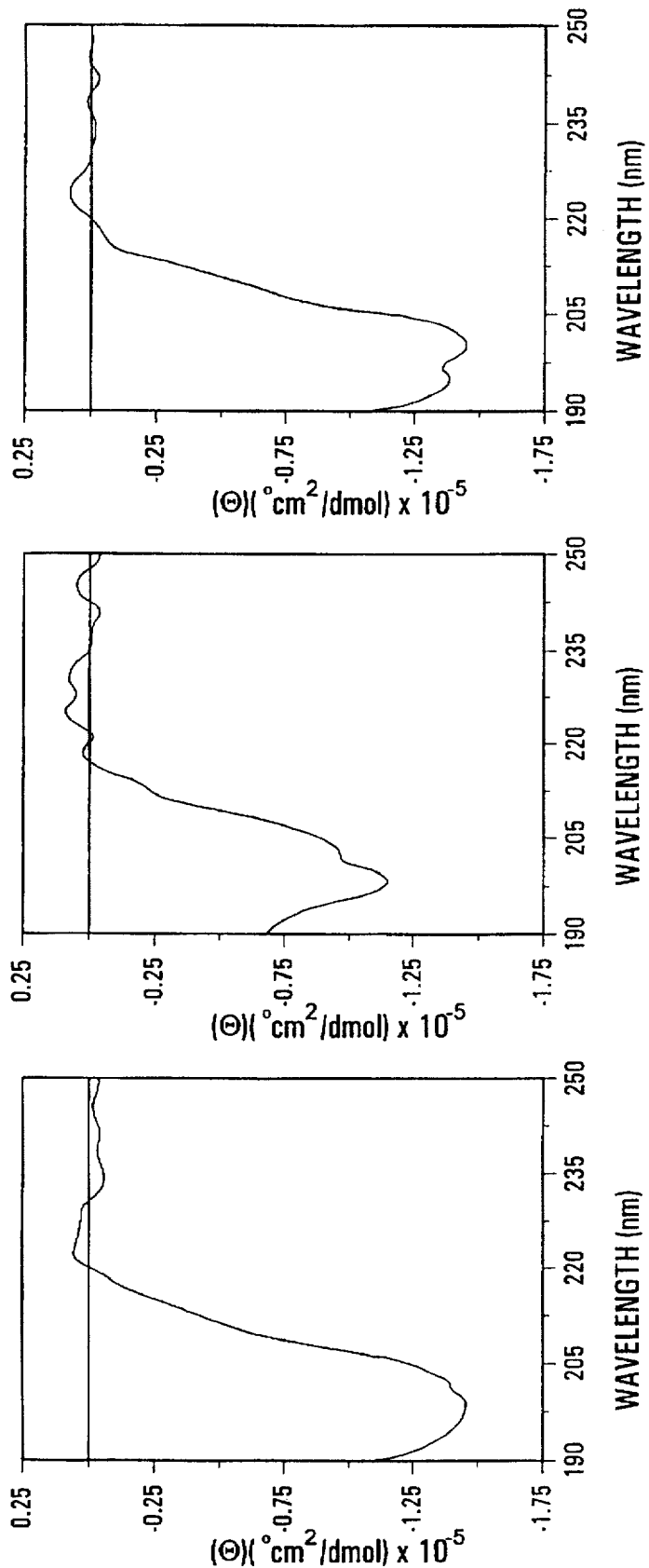

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 37 amino acids
        ( B ) TYPE: amino acid
        ( D ) TOPOLOGY: unknown ( x i ) SEQUENCE DESCRIPTION: SEQ ID NO:1:

```
Gly  Pro  Xaa  Gly  Pro  Xaa  Gly  Pro  Xaa  Gly  Pro  Xaa  Gly  Pro  Xaa  Gly
 1              5                        10                       15

Pro  Xaa  Gly  Pro  Xaa  Gly  Pro  Xaa  Gly  Glu  Phe  Tyr  Phe  Asp  Leu  Arg
              20                       25                       30

Leu  Lys  Gly  Asp  Lys
              35
```

( 2 ) INFORMATION FOR SEQ ID NO:2:

( i ) SEQUENCE CHARACTERISTICS:
        ( A ) LENGTH: 39 amino acids
        ( B ) TYPE: amino acid
        ( D ) TOPOLOGY: unknown ( x i ) SEQUENCE DESCRIPTION: SEQ ID NO:2:

```
Gly  Pro  Xaa  Gly  Pro  Xaa  Gly  Pro  Xaa  Gly  Pro  Xaa  Gly  Pro  Xaa  Gly
 1              5                        10                       15

Pro  Xaa  Gly  Pro  Xaa  Gly  Pro  Xaa  Gly  Val  Lys  Gly  Asp  Lys  Gly  Asn
              20                       25                       30

Pro  Gly  Trp  Pro  Gly  Ala  Pro
```

35

(2) INFORMATION FOR SEQ ID NO:3:

(i) SEQUENCE CHARACTERISTICS:
       (A) LENGTH: 24 amino acids
       (B) TYPE: amino acid
       (D) TOPOLOGY: unknown (xi) SEQUENCE DESCRIPTION: SEQ ID NO:3:

Gly Pro Xaa Gly Pro Xaa Gly Pro Xaa Gly Val Lys Gly Asp Lys Gly
   1               5                   10                  15

Asn Pro Gly Trp Pro Gly Ala Pro
                   20

(2) INFORMATION FOR SEQ ID NO:4:

(i) SEQUENCE CHARACTERISTICS:
       (A) LENGTH: 4 amino acids
       (B) TYPE: amino acid
       (D) TOPOLOGY: unknown (xi) SEQUENCE DESCRIPTION: SEQ ID NO:4:

Lys Lys Tyr Gly
   1

(2) INFORMATION FOR SEQ ID NO:5:

(i) SEQUENCE CHARACTERISTICS:
       (A) LENGTH: 39 amino acids
       (B) TYPE: amino acid
       (D) TOPOLOGY: unknown (xi) SEQUENCE DESCRIPTION: SEQ ID NO:5:

Gly Pro Xaa Gly Pro Xaa Gly Pro Xaa Gly Pro Xaa Gly Pro Xaa Gly
   1               5                   10                  15

Pro Xaa Gly Pro Xaa Gly Pro Xaa Gly Val Xaa Gly Xaa Xaa Gly Xaa
                   20                  25                  30

Pro Gly Trp Pro Gly Ala Pro
                   35

(2) INFORMATION FOR SEQ ID NO:6:

(i) SEQUENCE CHARACTERISTICS:
       (A) LENGTH: 39 amino acids
       (B) TYPE: amino acid
       (D) TOPOLOGY: unknown (xi) SEQUENCE DESCRIPTION: SEQ ID NO:6:

Gly Pro Xaa Gly Pro Xaa Gly Pro Xaa Gly Pro Xaa Gly Pro Xaa Gly
   1               5                   10                  15

Pro Xaa Gly Pro Xaa Gly Pro Xaa Gly Val Xaa Gly Xaa Xaa Gly Xaa
                   20                  25                  30

Pro Gly Trp Pro Gly Ala Pro
                   35

(2) INFORMATION FOR SEQ ID NO:7:

(i) SEQUENCE CHARACTERISTICS:
       (A) LENGTH: 4 amino acids
       (B) TYPE: amino acid
       (D) TOPOLOGY: unknown (xi) SEQUENCE DESCRIPTION: SEQ ID NO:7:

Xaa Lys Xaa Gly ( 2 ) INFORMATION FOR SEQ ID NO:8:

( i ) SEQUENCE CHARACTERISTICS:
    ( A ) LENGTH: 4 amino acids
    ( B ) TYPE: amino acid
    ( D ) TOPOLOGY: unknown ( x i ) SEQUENCE DESCRIPTION: SEQ ID NO:8:

Xaa Xaa Xaa Gly
1

( 2 ) INFORMATION FOR SEQ ID NO:9:

( i ) SEQUENCE CHARACTERISTICS:
    ( A ) LENGTH: 24 amino acids
    ( B ) TYPE: amino acid
    ( D ) TOPOLOGY: unknown ( x i ) SEQUENCE DESCRIPTION: SEQ ID NO:9:

Gly Pro Xaa Gly Pro Xaa Gly Pro Xaa Gly Pro Xaa Gly Pro Xaa Gly
1               5                   10                  15
Pro Xaa Gly Pro Xaa Gly Pro Xaa
            20

( 2 ) INFORMATION FOR SEQ ID NO:10:

( i ) SEQUENCE CHARACTERISTICS:
    ( A ) LENGTH: 4 amino acids
    ( B ) TYPE: amino acid
    ( D ) TOPOLOGY: unknown ( x i ) SEQUENCE DESCRIPTION: SEQ ID NO:10:

Gly Pro Xaa Gly
1

( 2 ) INFORMATION FOR SEQ ID NO:11:

( i ) SEQUENCE CHARACTERISTICS:
    ( A ) LENGTH: 30 amino acids
    ( B ) TYPE: amino acid
    ( D ) TOPOLOGY: unknown ( x i ) SEQUENCE DESCRIPTION: SEQ ID NO:11:

Pro Pro Gly Pro Pro Gly Pro Pro Gly Pro Pro Gly Pro Pro Gly Pro
1               5                   10                  15
Pro Gly Pro Pro Gly Pro Pro Gly Pro Pro Gly Pro Pro Gly
            20                  25                  30

( 2 ) INFORMATION FOR SEQ ID NO:12:

( i ) SEQUENCE CHARACTERISTICS:
    ( A ) LENGTH: 60 amino acids
    ( B ) TYPE: amino acid
    ( D ) TOPOLOGY: unknown ( x i ) SEQUENCE DESCRIPTION: SEQ ID NO:12:

Pro Pro Gly Pro Pro Gly Pro Pro Gly Pro Pro Gly Pro Pro Gly Pro
1               5                   10                  15
Pro Gly Pro Pro Gly Pro Pro Gly Pro Pro Gly Pro Pro Gly Pro Pro
            20                  25                  30
Gly Pro Pro Gly Pro Pro Gly Pro Pro Gly Pro Pro Gly Pro Pro Gly
        35                  40                  45
Pro Pro Gly Pro Pro Gly Pro Pro Gly Pro Pro Gly (2) INFORMATION FOR SEQ ID NO:13:

(i) SEQUENCE CHARACTERISTICS:
　　　　(A) LENGTH: 4 amino acids
　　　　(B) TYPE: amino acid
　　　　(D) TOPOLOGY: unknown (xi) SEQUENCE DESCRIPTION: SEQ ID NO:13:

Lys  Lys  Xaa  Gly
　　　1

MILD SOLID-PHASE SYNTHESIS OF ALIGNED, BRANCHED TRIPLE-HELICAL PEPTIDES

This is a division of application Ser. No. 08/534,342, filed Sep. 27, 1995, (U.S. Pat. No. 5,576,419) which, in turn, is a continuing application of Ser. No. 08/085,633, filed Jun. 30, 1993 (abandoned).

FIELD OF THE INVENTION

The present invention is directed to aligned, branched triple-helical peptides and the solid-phase synthesis of such peptides. More specifically, the invention is directed to the solid-phase synthesis of such peptides without strong or repetitive acidolysis.

BACKGROUND OF THE INVENTION

Several pathological conditions, such as diabetes mellitus and tumor cell metastasis, require interactions of proteins, glycosaminoglycans (GAGs), or cells with the triple-helical regions of native collagens. For example, tumor cell metastasis involves the adhesion and motility of tumor cells on extracellular matrix components such as laminin and collagen. The relative importance of collagen primary, secondary, and tertiary structure on these interactions has not been ascertained. To elucidate the roles of collagen structures on protein, GAG, and cell activities, single-stranded and triple-helical synthetic peptides need to be studied. To accomplish this, a general synthetic peptide methodology needs to be developed by which the importance of collagen triple-helical structure on biological activities can be evaluated. This methodology should also allow for incorporation of post-translationally modified amino acids, e.g. glycosylated amino acid residues, as types II and IV collagen are glycosylated.

Collagens are composed of three α chains of primarily repeating Gly-X-Y triplets, which induces each α chain to adopt a left-handed polyPro II helix. Three left-handed chains then intertwine to form a right-handed super-helix. Homotrimeric collagens (i.e., types II and III) have three α chains of identical sequence, whereas heterotrimeric collagens have two α chains of identical sequence (designated α1) and one α chain of differing sequence (designated α2) (i.e., type I) or three α chains of differing sequence (designated α1, α2, and α3) (i.e., type VI). Homotrimeric triple-helical polypeptides of defined molecular weight were created initially by solid-phase incorporation of tertiary-amyloxycarbonyl-X-Y-Gly tripeptides (prepared in solution), hydrogen fluoride cleavage, and interchain association in aqueous acetic acid. See, for example, S. Sakakibara et al., Bull. Chem. Soc. Jpn. 41, 1273 (1968). The most thermally stable triple-helices were formed with repeating Pro-Pro-Gly or Pro-Hyp-Gly triplets, with increased thermal stability resulting from Hyp versus Pro in the Y position. See, for example, J. Engel et al., Biopolymers 16, 601 (1977) and R. W. Webber et al., Helv. Chim. Acta 61, 701 (1978).

To more fully understand the subtleties of collagen structure, it is desirable to insert sequences other than Gly-Pro-Pro or Gly-Pro-Hyp within a triple-helix and correlate the effects of these sequences on triple-helical structure and biological activity. Such sequences should be aligned in the triple-helical peptide as they would be in native collagens. To ensure proper alignment of three peptide strands in a triple-helix, a branching protocol was developed for liquid-phase peptide synthesis by Heidemann and coworkers. See, for example, W. Roth et al., Makromol. Chem. 180, 905 (1979) and H.-P. Germann et al., Biopolymers 27, 157 (1988). The branch was introduced at the C-terminus of the synthetic peptide, consistent with the natural nucleation of collagen triple-helices from the C- to the N-terminus. A variation of this branching protocol was developed for solid-phase synthesis. See, for example, G. B. Fields et al., in *Innovation and Perspectives in Solid Phase Synthesis* (R. Epton, Ed.), pp. 241–260, Solid Phase Conference Coordination Ltd., Birmingham, U.K. (1990).

Such liquid- and solid-phase methodologies do not allow for the incorporation of glycosylated residues, as O-glycosidic bonds are not stable to repetitive moderate acidolysis and strong acid cleavage conditions. Glycosylated 5-hydroxy-L-lysine (Hyl) residues are found in regions of collagen-mediated biological activities such as cell adhesion and migration and heparin binding. Glycosylation also effects protein secondary structure, inducing β-turns in single-stranded peptides. Solid-phase peptide synthesis utilizing base-labile 9-fluorenylmethoxycarbonyl (Fmoc)-amino acids has become increasingly popular due to the fairly mild chemical conditions employed, which permit efficient incorporation of glycosylated residues. See, for example, G. B. Fields et al., Int. J. Peptide Protein Res. 35, 161 (1990). In addition, other acid labile residues, such as Trp or $^2$H-labeled amino acids (for NMR studies), are more efficiently incorporated by Fmoc chemistry than standard tertiary-butyloxycarbonyl (Boc) chemistry. Recent advances in Fmoc chemistry, including the development of three-dimensional orthogonal schemes, has permitted the design of synthetic protocols for the mild solid-phase synthesis of branched, triple-helical peptides. Triple-helical peptides synthesized under these mild conditions are far less likely to be contaminated by by-products as well as potentially incorporating the greatest variety of unusual and non-native amino acid residues.

SUMMARY OF THE INVENTION

The present invention provides synthetic triple-helical polypeptides. These synthetic polypeptides can be used as models for native polypeptides, such as collagen. The triple-helical polypeptide of the invention is of the formula:

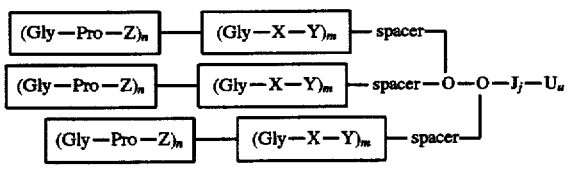

wherein Z is Hyp or Pro; and each X and Y is an amino acid such that $(Gly-X-Y)_m$ is a sequence of a collagen cell adhesion site, preferably a cell adhesion site of collagen type IV. Each of X and Y may be the same or different and each (Gly-X-Y) may be the same or different. That is, in any one branch of the triple helix, the sequence $(Gly-X-Y)_m$ has a Gly residue every third amino acid and two amino acids, X and Y, that may be the same or different between each Gly residue. Each (Gly-X-Y) may be the same of different in the $(Gly-X-Y)_m$ sequence. As used herein, the amino acids are referred to by their three letter designations. The single letter designations are not used unless so indicated. Thus, the single letter designations O, J, X, Y, etc. in the above formula are not used as single letter designations for one specific amino acid.

In the formula for the triple-helical polypeptide, O is an amino acid having a single side-chain amino group; J is an amino acid capable of acting as a chromophore, i.e., a chromophoric amino acid; and U is any amino acid, preferably Gly. Furthermore, j≧1, preferably j=1; u=0 or 1, such that U may be present or absent, preferably U is present (u=1); n≦30, preferably 3–8; m≦30, preferably 0–5, and more preferably 1–5; and m+n≦30. Thus, although each triple-helical molecule preferably includes a (Gly-Pro-Z) sequence and a (Gly-X-Y) sequence, this is not necessarily a requirement as long as the total number of such sequences combined is not greater than 30.

The (Gly-Pro-Z) sequence is capable of inducing a triple helix in each molecule. Thus, Z is chosen such that this occurs. As stated above, Z can be Hyp or Pro, preferably however, Z is Hyp. To form a branched triple helix, two amino acids (O residues) are required per molecule that have a single side-chain amino group, such as, for example, Lys and Orn. Preferably the amino acid O in the above formula is Lys. In particularly preferred embodiments of the present invention, the triple-helical polypeptide includes the sequence (Gly-Pro-Hyp)$_8$-Gly-Glu-Phe-Tyr-Phe-Asp-Leu-Arg-Leu-Lys-Gly-Asp-Lys (SEQ ID NO:1), (Gly-Pro-Hyp)$_8$-Gly-Val-Lys-Gly-Asp-Lys-Gly-Asn-Pro-Gly-Trp-Pro-Gly-Ala-Pro (SEQ ID NO:2), or (Gly-Pro-Hyp)$_3$-Gly-Val-Lys-Gly-Asp-Lys-Gly-Asn-Pro-Gly-Trp-Pro-Gly-Ala-Pro (SEQ ID NO:3).

The triple-helical polypeptides of the present invention also include at least one amino acid residue per molecule that is a chromophore. In this way, the concentration of the polypeptide can be easily determined. Any chromophoric amino acid can be used. Examples include, but are not limited to, Tyr, Trp, and nitrophenylalanine. Preferably, the chromophoric amino acid is Tyr.

The spacer in the triple-helical polypeptides of the present invention can be any alkyl chain ($C_1$ through $C_{20}$) substituted with an amino group and a carboxyl group. Such a spacer allows for flexibility in alignment of the three chains in the triple helix structure. Examples of such spacers include, but are not limited to 6-aminohexanoic acid, 4-aminobutyric acid, and 8-aminooctanoic acid. Preferably, the spacer is 6-aminohexanoic acid, referred to herein as Ahx.

The present invention is also directed to the supported intermediates used in the preparation of the triple-helical polypeptides of the invention. Thus, a supported branched polypeptide of the following formula is provided:

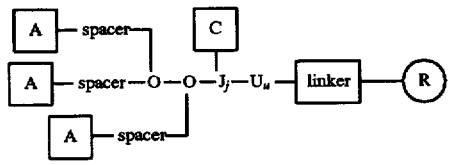

wherein: O is an amino acid having a single side-chain amino group; J is an amino acid capable of acting as a chromophore; and U is any amino acid as discussed above. Furthermore, u=0 or 1, and j≧1, preferably j=1. In this branched intermediate, A is an N$^\alpha$-amino protecting group capable of being removed under non-acidic conditions; C is a protecting group capable of withstanding the non-acidic conditions under which A is removed; the linker is capable of being removed using a non-strong acid mechanism; and R is a support material.

Preferably, A can be any amino protecting group that is capable of being removed using conditions that do not require acid. For example, A can be Fmoc, Mpc, Dts, Npys, Nvoc, Aloc, and Dde. Preferably, A is Fmoc. C is a protecting group that is resistant to removal under the conditions in which A is removed, and preferably is capable of being labilized, i.e., removed, under the same conditions as the linker. Thus the linker and C are chosen such that they are not disrupted when A is removed. They can be removed using a moderate acid, i.e., under mild acidic conditions. As used herein, a "mild," "moderate," and "non-strong" acid refer to an acid that can be used to prepare the triple-helical polypeptides of the present invention. Any such acid, whether it is an organic or inorganic acid, is chosen such that it does not disrupt O-glycosidic bonds during a 1–2 h treatment at a temperature of 25° C. Preferably, useable non-strong acids are those with an H$_0$ of −5 or higher, as defined by J. P. Tam et al., in The Peptides, Vol. 9 (S. Udenfriend and J. Meienhofer, Eds.), pp. 185–248, Academic Press, New York (1987). Examples of such acids include, but are not limited to, hydrochloric, acetic, sulfuric, and trifluoroacetic acid. More preferably, the non-strong acid of choice for removing the linker and protecting group C is trifluoroacetic acid (TFA).

Thus, C and the linker are chosen such that they are not affected when A is removed. Preferably, they are chosen such that they can be removed using the same non-strong acid conditions. Non-strong acid conditions for cleavage can include the use of a moderate or weak acid, photolysis, the use of palladium-catalyzed nucleophilic transfer, and the use of fluoride ion. Preferred C groups are Dcb, allyl, and tBu. Preferred linkers are allyl, HMP, and SASRIN™ (3-methoxy-4-hydroxymethylphenoxy). Other linkers are described by G. B. Fields et al., Int. J. Peptide Protein Res. 35, 161 (1990) and G. B. Fields et al., in Synthetic Peptides: A User's Guide (G. A. Grant, Ed.), pp. 77–183, W. H. Freeman and Co., New York (1992).

The support material can be any of a variety of support materials used for supported synthetic procedures. These support materials can be inorganic or organic. They can be solids, gels, glasses, membranes, proteins, etc. Examples of useable support materials are described by G. B. Fields et al., Int. J. Peptide Protein Res. 35, 161 (1990) and G. B. Fields et al., in Synthetic Peptides: A User's Guide (G. A. Grant, Ed.), pp. 77–183, W. H. Freeman and Co., New York (1992). Preferably, the support material is an organic polymeric material, such as crosslinked polystyrene, or a hybrid of crosslinked polystyrene and polyethylene glycol.

The present invention also provides a supported polypeptide of the formula:

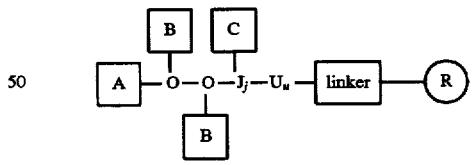

wherein: A is an N$^\alpha$-amino protecting group capable of being removed under non-acidic conditions; O is an amino acid having a single side-chain amino group; J is an amino acid capable of acting as a chromophore; and C is a protecting group capable of withstanding the conditions in which A and B are removed, as described above. As in the compounds discussed above U is any amino acid, which may be present or absent; and J is a chromophoric amino acid, at least one of which is present per molecule. Also, as discussed above, the linker is capable of being labilized using a non-strong acid mechanism; and R is a support material. Preferred groups are those discussed above. In this intermediate, B is a non-strong acid labile side-chain amino protecting group. In this context, "non-strong" acid is used as above. Preferably, B is Boc, Aloc, or Dde.

The present invention also provides a method of preparing a triple-helical polypeptide comprising: assembling a polypeptide on a support material using an $N^\alpha$-amino protecting group and non-acidic conditions; removing the side-chain amino protecting groups to form two N-termini under conditions that do not cleave the polypeptide from the support material or the optional side-chain protecting group from the chromophoric amino acid; removing the $N^\alpha$-amino protecting group to form a third N-terminus; incorporating a spacer group on the three N-termini; and assembling an amino acid sequence of interest on the spacer group. The polypeptide assembled in the first step includes two amino acid residues each having a single side-chain amino protecting group; and at least one chromophoric amino acid optionally having a single side-chain protecting group. Preferably, the method further includes a step of assembling a (Gly-Pro-Z)$_n$ on the sequence of interest, wherein Z is Hyp or Pro and n≦30. More preferably, the step of assembling an amino acid sequence of interest on the spacer group comprises: assembling the sequence using an $N^\alpha$-amino protecting group and non-acidic conditions; and removing the $N^\alpha$-amino protecting group using DBU prior to assembling the (Gly-Pro-Z)$_n$ sequence.

In preferred embodiments of the method, the $N^\alpha$-amino protecting group is Fmoc. The side-chain amino protecting group can be removed under moderate acid conditions, such as Boc, using hydrazine, such as Dde, using a palladium-catalyzed nucleophilic transfer, such as Aloc. The method is applicable for the preparation of polypeptides containing collagen-derived sequences; however, other sequences of interest can be incorporated into polypeptides. For example, this can include sequences known for proteolysis, and cell adhesion sequences, such as Arg-Gly-Asp.

The present invention results from the study of different side-chain and linker chemistries, solvation conditions, and/or acylating agents for the highly efficient, 9-fluorenylmethoxycarbonyl (Fmoc)-based solid-phase syntheses of triple-helical, collagen-model peptides. Specifically, the Fmoc-based two- and three-dimensional orthogonal syntheses and characterizations of four triple-helical polypeptides (THPs), three of which incorporate cell adhesion sequences from the α1 chain of type IV collagen, is described. The sequences from type IV collagen are residues 531–543, which promote human keratinocyte adhesion and rabbit corneal epithelial cell adhesion and migration, and residues 1263–1277, which support adhesion, spreading, and motility of highly metastatic mouse melanoma cells. For all THPs, three nascent peptide chains are C-terminal-linked through one $N^\alpha$-amino and two $N^\epsilon$-amino groups of Lys, while repeating Gly-Pro-Hyp triplets induce triple-helicity. Highly efficient assemblies are achieved by in situ 2-(1H-benzotriazole-1-yl)-1,1,3,3-tetramethyluronium hexafluorophosphate (HBTU)-mediated couplings and 1,8-diazabicyclo[5.4.0]undec-7-ene (DBU)-mediated Fmoc group removal. Also provided is a generally applicable solid-phase methodology for the synthesis of triple-helical polypeptides incorporating native collagen sequences. The synthetic strategies presented herein will allow for the study of both structure and biological activity of specific collagen sequences in homotrimeric and heterotrimeric forms.

BRIEF DESCRIPTION OF THE DRAWINGS

FIG. 1: General scheme for synthesis of branched, triple-helical peptides. Ahx is 6-aminohexanoic acid (SEQ ID NO:4).

FIGS. 8a–c: CD spectra of (left) THP-1 at 15° C., (middle) THP-3 at 25° C., and (right) THP-4 at 25° C. in 0.5–1% aqueous HOAc, pH 2.4. Conditions are given under Experimental Section.

DETAILED DESCRIPTION

Figure 2A:
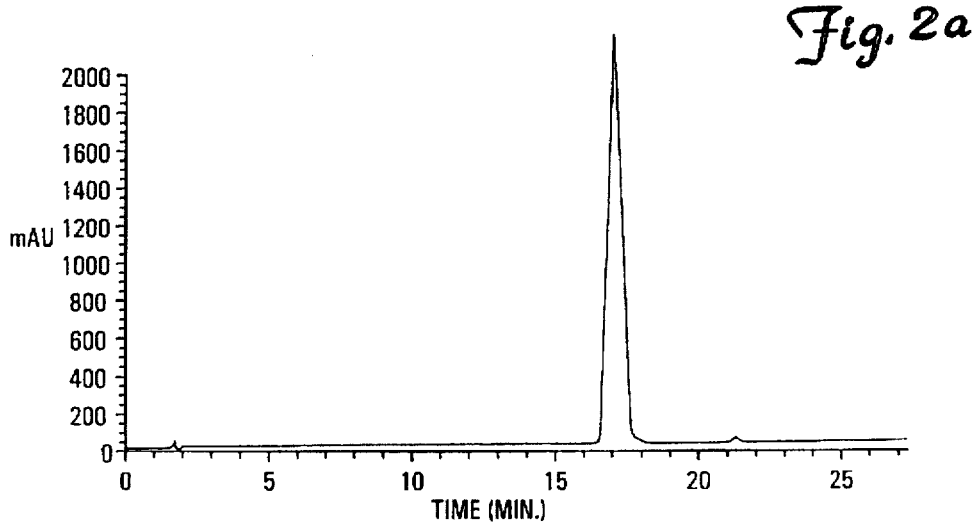
FIGS. 2a–c: Analytical reversed-phase HPLC elution profiles of purified THP-1 (top), THP-3 (middle), and THP-4 (bottom). Gradient was from 20–80% B in 30 min for THP-1 and 0–60% B in 45 min for THP-3, where A was 0.1% TFA in H$_2$O and B was 0.08% TFA in acetonitrile. Gradient was from 0–100% B in 30 min for THP-4, where A was 0.1M NaH$_2$PO$_4$ adjusted to pH 3.0 with 0.1M phosphoric acid and B was methanol. Other conditions are given under Experimental Section.

The invention has been described with reference to various specific and preferred embodiments and will be further described by reference to the following detailed examples. It is understood, however, that there are many extensions, variations, and modifications on the basic theme of the present invention beyond that shown in the examples and description, which are within the spirit and scope of the present invention.

I. Experimental Section

Materials

All amino acids are of the L-configuration except where noted. N,N-diisopropylethylamine (DIEA), 1-methyl-2-pyrrolidinone (NMP), piperidine, and trifluoroacetic acid (TFA) were from Applied Biosystems, Inc. (Foster City, Calif.), acetic acid (HOAc), acetonitrile, N,N-dimethylformamide (DMF), dichloromethane (DCM), and 4-(dimethylamino)pyridine (DMAP) from Fisher, D-Hyp and 1-fluoro-2,4-dinitrophenyl-5-L-alaninamide (FDAA) from Sigma, 1,8-diazabicyclo[5.4.0]undec-7-ene (DBU), N,N'-diisopropylcarbodiimide (DIPCDI), tetrakis (triphenylphosphine)palladium(0) [(Ph$_3$P)$_4$Pd], 1,2-ethanedithiol (EDT), and sinapinic acid (3,5-dimethoxy-4-hydroxycinnamic acid) from Aldrich, polyethylene glycol-copoly(styrene-1%-divinylbenzene) resin (HCl.PEG-PS resin) (sub. level=0.18 mmol/g), 4-hydroxymethylphenoxyacetic acid pentafluorophenyl ester (HMPA-OPfp), and Fmoc-Gly-HMP resin (sub. level= 0.43 mmol/g) from Millipore Corporation (Bedford, Mass.), Boc-Gly-PAM resin (sub. level=0.48 mmol/g) from Bachem (Torrance, Calif.), Fmoc-Tyr(tBu)-SASRIN resin (sub. level=0.55 mmol/g), 4-methylbenzhydrylamine (MBHA) resin (sub. level=0.80 mmol/g), and Gly-Pro-Hyp from Bachem Biosciences (Philadelphia, Pa.), 1-hydroxybenzotriazole (HOBt) from Novabiochem (La Jolla, Calif.), and 2-(1H-benzotriazole-1-yl)-1,1,3,3-tetramethyluronium hexafluorophosphate (HBTU) from Richelieu Biotechnologies (St.-Hyacinthe, Quebec). Fmoc-Hyp(tBu) and Fmoc-Lys(Dde) were from Novabiochem, 4-trityloxy-Z-but-2-enyloxyacetic acid (allyl linker) and Fmoc-Tyr(Al) from Propeptide, and Fmoc-6-aminohexanoic acid (Fmoc-Ahx) and Fmoc-Nle from Advanced ChemTech (Louisville, Ky.); all other Fmoc-amino acids were from Bachem Biosciences or Millipore.

Preparation of Fmoc-Gly-Pro-Hyp

Fmoc-Gly-Pro-Hyp was synthesized from Gly-Pro-Hyp as follows: 3.0 g Gly-Pro-Hyp (10.5 mmol) was dissolved in 54 mL Na$_2$CO$_3$—H$_2$O (1:9) and stored at 4° C. 4.05 g 9-fluorenylmethyl succinimidyl carbonate (12.0 mmol) was dissolved in 45 mL dimethoxyethane and stirred at 4° C. The aqueous Na$_2$CO$_3$ solution was added slowly to the dimethoxyethane solution, and the reaction proceeded for 2.5 h at 4° C. and 21 h at room temperature. The solution was filtered, and 360 mL H$_2$O was added to the filtrate. The aqueous layer was extracted with 300 mL of diethyl ether, acidified to pH 2 with concentrated HCl, reduced to half volume at 80° C. under reduced pressure, and stored at 4° C. for 24 h. The aqueous layer was decanted from the oily precipitate, reduced to ~30 mL at 81° C. under reduced pressure, and stored at 4° C. for 24 h. The aqueous layer was decanted from the oily precipitate. Both oily precipitates were dissolved in a total of 20 mL methanol, then 250 mL ethyl acetate was added. A white residue was recovered by evaporation at 73° C. for 1 h under reduced pressure; yield 3.23 g (6.39 mmol, 60.6%). The identity of the product as Fmoc-Gly-Pro-Hyp and its homogeneity was verified by thin layer chromatography [chloroform-methanol-HOAc (95:20:3)], scanning UV spectroscopy, and Edman degradation sequence analysis.

Preparation of Fmoc-Gly-HMP-PEG-PS Resin 4.0 g HCl.PEG-PS resin (0.72 mmol) was washed with DCM, neutralized with 60 mL DIEA-DCM for 0.5 h, and washed with DCM and DMF. 0.917 g HMPA-OPfp (2.46 mmol) and 0.441 g HOBt (2.88 mmol) were dissolved in 60 mL DMF and added to the resin. Coupling proceeded for 14.5 h. The resin was washed 3 times with DMF; ninhydrin analysis was negative. 0.856 g Fmoc-Gly (2.88 mmol) and 0.035 g DMAP (0.29 mmol) were dissolved in 60 mL DMF and added to the resin. After shaking for 5 min, 0.491 mL DIPCDI (2.88 mmol) was added, and esterification proceeded for 4.5 h. The resin was washed 2 times with DMF and 1 time with DCM and stored under vacuum overnight. The substitution level of Fmoc-Gly-HMP-PEG-PS was determined by spectrophotometric analysis to be 0.092 mmol/g.

Preparation of Fmoc-Gly-Allyl Resin 0.848 g Fmoc-Nle (2.4 mmol) was coupled to 2.0 g MBHA resin (1.6 mmol) with 0.367 g HOBt (2.4 mmol) and 0.373 mL DIPCDI (2.4 mmol) in 20 mL DCM-DMF (1:1) for 2.3 h. The resin was washed 3 times with DMF, deprotected with 20 mL piperidine-DMF (1:1) for 30 min, and washed 3 times with DMF. 1.82 g allyl linker (3.2 mmol) was coupled to the resin with 0.489 g HOBt (3.2 mmol) and 0.497 mL DIPCDI (3.2 mmol) in 20 mL DMF for 18.5 h. The resin was washed 1 time with DMF and 2 times with DCM, deprotected twice with 20 mL TFA-DCM (9:1), first for 20 min, then for 10 min, washed 3 times with DCM, neutralized with 20 mL DIEA-DCM (1:9) for 15 min, and washed 1 time with DCM and 2 times with DMF. 1.43 g Fmoc-Gly (4.8 mmol) was esterified to the allyl resin with 0.735 g HOBt (4.8 mmol), 0.746 mL DIPCDI (4.8 mmol), and 0.059 g DMAP (0.48 mmol) in 20 mL DMF for 6.5 h. The resin was washed 1 time with DMF and 2 times with DCM and stored under vacuum overnight.

Preparation of [N-tris(Fmoc-Ahx)-Lys-Lys]-Tyr(Al)-Gly-Allyl Resin (SEQ ID NO:13)

Fmoc-Tyr(Al), Fmoc-Lys(Boc), and Fmoc-Lys(Boc) were coupled to Fmoc-Gly-allyl resin with 1.40 mmol Fmoc-amino acid, 0.215 g HOBt (1.40 mmol), and 0.218 ml DIPCDI (1.40 mmol) in 20 mL DMF for 2–4 h. Both Fmoc-Lys(Boc) residues were double coupled. Fmoc removal was by 20 mL piperidine-DMF (1:1) for 0.5 h. The peptide-resin was washed 3 times with DMF after each coupling and deprotection, then 1 time with DCM prior to removal of the Boc groups. The N$^\epsilon$-amino Boc groups were removed by treatment of Fmoc-Lys(Boc)-Lys(Boc)-Tyr(Al)-Gly-allyl (SEQ ID NO:8) resin with 20 mL TFA-DCM (1:1) for 0.5 h. The peptide-resin was washed 3 times with DCM, neutralized with 20 mL DIEA-DCM (1:9) for 0.5 h, washed 2 times with DCM and 1 time with DMF, and Fmoc-deprotected as described above. Fmoc-Ahx was double coupled for 2.5–3 h as described above using 4.10 mmol of Fmoc-Ahx (1.45 g), HOBt (0.630 g), and DIPCDI (0.638 mL). The substitution level was determined by fulvene-piperidine analysis to be 0.181 mmol/g.

Preparation of Other [N-tris(Fmoc-Ahx)-Lys-Lys]-Tyr(C)-U Branched Resins

Fmoc-Tyr and Fmoc-Lys derivatives were coupled manually as described above. Fmoc-Tyr(Dcb) and Fmoc-Lys (Boc) were incorporated on Boc-Gly-PAM resin, Fmoc-Tyr (tBu) and Fmoc-Lys(Aloc) on Fmoc-Gly-HMP-PEG-PS resin, and Fmoc-Lys(Dde) on Fmoc-Tyr(tBu)-SASRIN resin. Fmoc removal was by 20 mL piperidine-DMF (1:1) for 0.5 h. All couplings and Fmoc deprotections were monitored by qualitative ninhydrin analysis. The N$^\epsilon$-amino Boc groups were removed by TFA, Aloc groups by (Ph$_3$P)$_4$Pd, and Dde groups by hydrazine. N$^\epsilon$-amino group deprotection was monitored quantitatively by Edman degradation sequence analysis. Fmoc-Ahx was single or double coupled for 2.5–3 h manually using 3-fold excesses of Fmoc-Ahx and HOBt, a 2.5-fold excess of HBTU, and a 5.5-fold excess of DIEA. The substitution level was determined by spectrophotometric analysis to be 0.57 mmol/g for [N-tris(Fmoc-Ahx)-Lys-Lys]-Tyr(Dcb)-Gly-PAM (SEQ ID NO:7) resin, 0.12 mmol/g for [N-tris(Fmoc-Ahx)-Lys-Lys]-Tyr(tBu)-Gly-HMP-PEG-PS (SEQ ID NO:7) resin, and 0.83 mmol/g for [N-tris(Fmoc-Ahx)-Lys-Lys]-Tyr(tBu)-SASRIN resin.

Peptide Synthesis and Purification

Incorporation of individual amino acids was by Fmoc solid-phase methodology on an Applied Biosystems 431A Peptide Synthesizer using cycles described by C. G. Fields et al., Peptide Res. 4, 95 (1991) and C. G. Fields et al., Anal. Biochem. 203, 245 (1992), which are incorporated herein by reference. For Fmoc removal, a 10 mL solution of DBU-piperidine-NMP (1:1:48) was used instead of piperidine- NMP (1:4) for 3 and 7 min. Incorporation of Fmoc-Gly-Pro-Hyp tripeptides was performed manually in a shaker as follows: The Fmoc-peptide-resin (0.10 mmol) was deprotected with 10 mL DBU-piperidine-DMF (1:1:48) for 0.5 h and washed 3 times with DMF. 0.202 g Fmoc-Gly-Pro-Hyp (0.40 mmol) and 0.061 g HOBt (0.40 mmol) were dissolved in 10 mL 0.035M HBTU-DMF. 0.131 mL DIEA (0.75 mmol) was added, and the solution reacted with the resin for 2.5 h. The Fmoc-peptide-resin was washed 3 times with DMF. Deprotection and coupling steps were repeated 7 times.

THP-1 (see Table I for sequence, wherein the single letter designations for amino acids are used) was cleaved and side-chain deprotected by treatment of the peptide-resin with TFMSA for 2.5 h as described by G. B. Fields et al., in *Synthetic Peptides: A User's Guide* (G. A. Grant, Ed.), pp. 77–183, W. H. Freeman and Co., New York (1992), which is incorporated herein by reference. The precipitated crude product was dissolved in 2 mL $H_2O$-acetonitrile (1:1) and purified by preparative reversed-phase HPLC. THP-2 (see Table I for sequence) was side-chain deprotected by TFA-EDT-$H_2O$ (92.5:2.5:5) for 1 h, washed with DCM, and liberated from the resin by treatment with 0.074 g $(Ph_3P)_4Pd$ (0.065 mmol) for 20 h as described by P. Lloyd-Williams et al., Tetrahedron Lett. 32, 4707 (1991). The crude product was dissolved in 0.5N aqueous HCl, extracted with diethyl ether and DCM, and purified by size exclusion chromatography and semipreparative reversed-phase HPLC. THP-3 and THP-4 (see Table I for sequences) were cleaved and side-chain deprotected by treatment of the peptide-resins with TFA-$H_2O$ (95:5) for 2 and 1 h, respectively. Resins were filtered and rinsed with 4 mL TFA, and the combined filtrate and wash reduced under vacuum at room temperature to 4).5 mL, diluted with 2–4 mL $H_2O$, and purified by preparative reversed-phase HPLC.

Preparative reversed-phase HPLC was performed on a BECKMAN System Gold or a Rainin AutoPrep System with a REGIS Chemical ODS C-18 column (10 μm particle size, 60 Å pore size, 250×21.1 mm). The elution gradient was 30–100% B in 70 min at a flow rate of 5.0 mL/min for THP-1, 12–60% B in 35 min at a flow rate of 5.6 mL/min for THP-3, and 30–100% B in 60 min at a flow rate of 5.0 mL/min for THP-4, where A was 0.1% TFA in $H_2O$ and B was 0.08% TFA in acetonitrile. Detection was at 229 nm. Semipreparative HPLC was performed on a RAININ AutoPrep System with a Dynamax C-18 column (12 μm particle size, 300 Å pore size, 250×10 mm). The elution gradient was 0–60% B in 45 min at a flow rate of 2.0 mL/min, where A was 0.1% TFA in $H_2O$ and B was 0.08% TFA in acetonitrile. Detection was at 229 nm. Analytical reversed-phase HPLC was performed on a Hewlett-Packard 1090 Liquid Chromatograph equipped with an ODS Hypersil C-18 column (5 μm particle size, 100×2.1 mm). 10 μL from preparative HPLC fractions were loaded onto the column. The elution gradient was 0–60% B in 20 min at a flow rate of 0.3 mL/min, where A and B were the same as for preparative HPLC. Diode array detection was at 220, 254, and 280 nm. Pure fractions were pooled and lyophilized. For THP-4, analytical HPLC was also performed with a Vydac $C_4$ reversed-phase column (5 μm particle size, 250×4.6 mm) or a Bio-Rad Bio-Gel TSK-phenyl-5-PW hydrophobic interaction column (10 μm particle size, 1000 Å pore size, 75×7.5 mm). Solvent A was 1.7M ammonium phosphate plus 0.1M sodium phosphate, pH 7 and solvent B was 0.1M sodium phosphate, pH 7 for hydrophobic interaction HPLC.

TABLE I

Collagen Sequences Synthesized As Triple-Helical Polypeptides

| Peptide | Collagen Chain | Sequence[a] | Branching Chemistry[b] | Yield (%) | $T_m$ (°C.) |
|---|---|---|---|---|---|
| THP-1 | α1(IV) 531–543 | (Gly—Pro—Hyp)₈Gly—Glu—Phe—Try—Phe—Asp—Leu—Arg—Leu—Lys—Gly—Asp—Lys (SEQ ID NO: 1) | A = Fmoc<br>B = Boc<br>C = Dcb<br>linker = PAM | 39.2 | 53.0 |
| THP-2 | α1(IV) 1263–1277 | (Gly—Pro—Hyp)₈Gly—Val—Lys—Gly—Asp—Lys—Gly—Asn—Pro—Gly—Trp—Pro—Gly—Ala—Pro (SEQ ID NO: 2) | A = Fmoc<br>B = Boc<br>C = Allyl<br>linker = Allyl | 4.7 | 58.5 |
| THP-3 | | (Gly—Pro—Hyp)₈ (SEQ ID NO: 9) | A = Fmoc<br>B = Aloc<br>C = tBu<br>linker = HMP | 13.5 | 42.5 |
| THP-4 | α1(IV) 1263–1277 | (Gly—Pro—Hyp)₃Gly—Val—Lys—Gly—Asp—Lys—Gly—Asn—Pro—Gly—Trp—Pro—Gly—Ala—Pro (SEQ ID NO: 3) | A = Fmoc<br>B = Dde<br>C = tBu<br>linker = SASRIN™ | 13.6 | 35.0 |

[a]P* = Hyp.
[b]See FIG. 1 for location of A, B, C, and linker.

THP Analyses

Edman degradation sequence analysis was performed on an Applied Biosystems 477A Protein Sequencer/120A Analyzer for both solid-phase and "embedded" (non-covalent) sequencing as described by C. G. Fields et al., Anal. Biochem. 203, 245 (1992) and C. G. Fields et al., Peptide Res. 6, 39 (1993), which are incorporated herein by reference. Fulvene-piperidine concentrations (301 nm) and scanning UV spectra (200–320 nm) were determined with a BECKMAN DU-70 Spectrophotometer. Amino acid analyses were performed on a BECKMAN 6300 Analyzer with a sulfated polystyrene cation-exchange column (0.4cm×25 cm). Peptides were hydrolyzed with 6N aqueous HCl at 110° C. for 18–48 h. Electrospray mass spectrometric (ES-MS) methods have been described by C. G. Fields et al., Peptide Res. 6, 39 (1993), which is incorporated herein by reference. Fast atom bombardment (FAB) MS was performed on a VG 7070E-HF with a glycerol matrix and laser desorption time-of-flight (LD-TOF) MS with both a breadboard and prototype matrix-assisted TOF mass spectrometer from Millipore Corporation (Milford, Mass.) with a sinapinic acid matrix [saturated solution of 10 mg/mL sinapinic acid dissolved in acetonitrile-$H_2O$ (1:3) containing 0.1% TFA]. THPs were $^3$H-labeled by reductive methylation [N. Jentoft et al., J. Biol. Chem. 254, 4359 (1979)] with $NaCNBH_3$ and [$^3$H]formaldehyde, desalter over a Sephadex G-50 column (50×1.5 cm) in PBS, pH 7.4, and analyzed by size-exclusion chromatography (SEC). CD spectroscopy was performed on a Jasco 710 spectropolarimeter using a 100 or 200 µL, 0.1 mm cell. The THP concentrations (determined spectrophotometrically) in 1–5% aqueous HOAc, pH 2.4 were [THP-1]=0.16 mM, [THP-2]=0.084 mM, [THP-3]= 0.068 mM, and [THP-4]=0.015 mM. Spectra were recorded by accumulating 5 scans at 0.5 nm intervals (response of 1 sec). Thermal transitions were examined by measuring the molar ellipticity ([θ]) at 225 nm from 15°–85° C.

Racemization of Hyp During Fmoc-Gly-Pro-Hyp Coupling

Fmoc-Gly-Pro-Hyp was coupled to Gly-HMP resin and deprotected under the same conditions as described in Peptide Synthesis and Purification. Gly-Pro-Hyp-Gly (SEQ ID NO:10) was liberated from the resin with a 1 h treatment of TFA-water (95:5), precipitated with methyl tBu ether, and hydrolyzed for 3, 6, 9, 20, and 46 h as described in Peptide Analyses. Two different Gly-Pro-Hyp-Gly (SEQ ID NO:10) concentrations were used. Racemization studies were performed by derivatizing samples with FDAA as described [J. G. Adamson et al., Anal. Biochem. 202, 210 (1992)] and eluting DNPA-amino acids by analytical HPLC (see Peptide Synthesis and Purification) with an elution gradient of 5–20% B in 70 min at a flow rate of 0.5 mL/min. Detection was at 340 nm.

Melanoma Cell Adhesion and Spreading

K1735 M4 tumor cell adhesion and spreading assays were as described previously [M. K. Chelberg et al., J. Cell Biol. 111, 261 (1990)] with minor alterations. Peptides were dissolved in PBS and adsorbed directly onto 96-well polystyrene Immulon 1 plates (Dynatech Laboratories Inc., Chantilly, Va.) overnight at 37° C. Nonspecific binding sites were blocked with 5 mg/mL bovine serum albumin in adhesion media [Dulbecco's modified Eagle's medium containing 20 mM 4-(2-hydroxyethyl)-1-piperazineethanesulfonic acid] for 2 h at 37° C. Tumor cells were released from tissue culture flasks with 37° C. PBS containing 10 mM EDTA and washed several times with adhesion media. Cells were labeled overnight with 1 µCi/mL [$^3$H]thymidine (New England Nuclear, Boston, Mass.) for adhesion assays. Cells were added to the plate wells at a density of 50,000 cells/mL in a total volume of 100 µL and adhered for 1 h at 37° C. For adhesion assays wells were washed several times with adhesion media and remaining cells lysed and radioactivity determined as described [M. K. Chelberg et al., J. Cell Biol. 111, 261 (1990)]. For spreading assays wells were fixed and stained using DiffQuik reagents (Baxter) and photographed with a Nikon MF-15 camera mounted on a Nikon Diaphot inverted microscope at 200× magnification. Cell spreading was quantitated by an Optomax System IV image analyzer equipped with a Hitachi Monitor. The efficiency of peptide adsorption to the Immulon plates was determined as described [M. K. Chelberg et al., J. Cell Biol. 111, 261 (1990)] using $^3$H- or $^{125}$I-labeled peptide.

II. Design, Synthesis, and Characterization of Triple-Helical Polypeptides

Figure 2B:
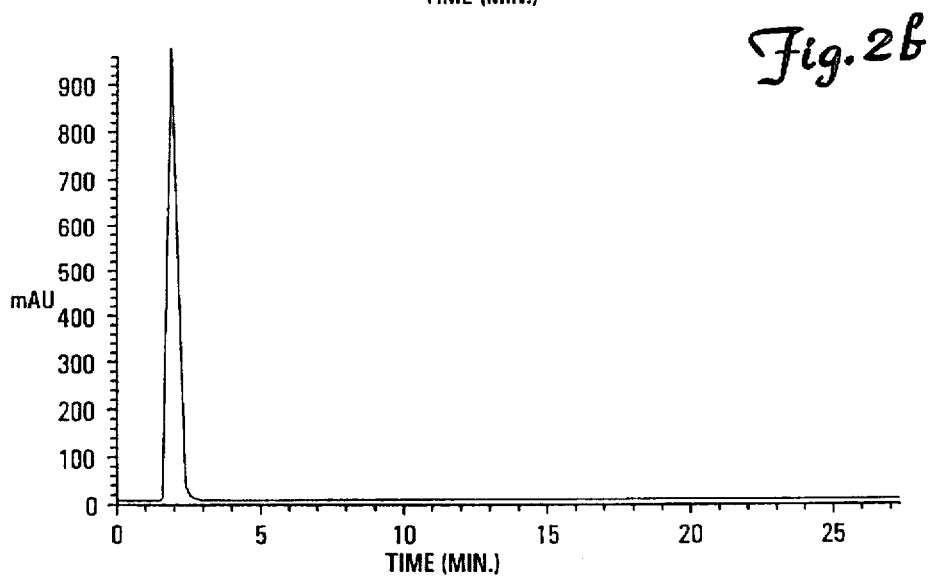
Figure 2C:
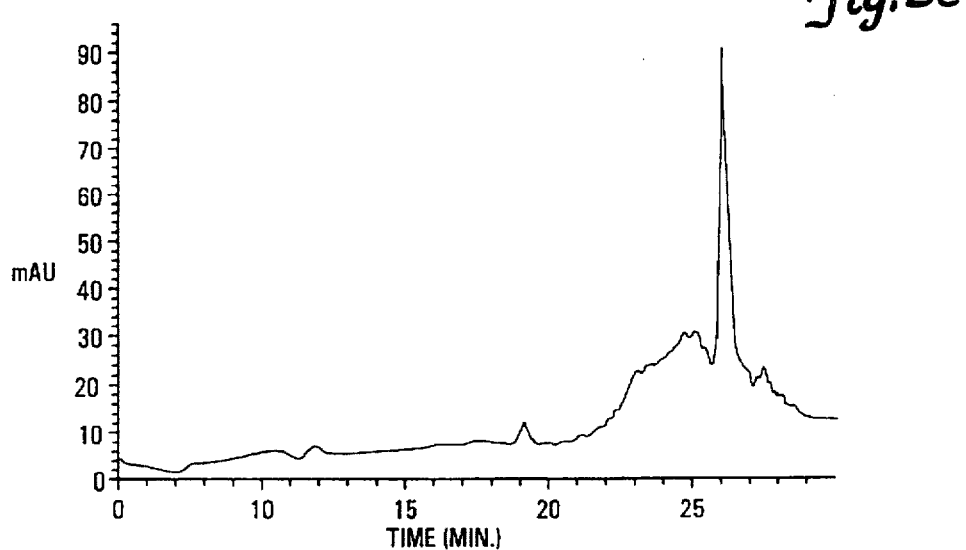

Branching of three peptide strands from one initial chain requires three different protecting group strategies (FIG. 1): $N^\alpha$-amino protection (A), Lys $N^\epsilon$-amino side-chain protection (B), which must be stable to the $N^\alpha$-amino group removal conditions, and $C^\alpha$-carboxyl protection (linker), which must be stable to both the $N^\alpha$- and $N^\epsilon$-amino protecting group removal conditions. Four different synthetic schemes were employed, with the only common protecting group strategy being Fmoc for A (see Table I). The 531–543 sequence of α1(IV) collagen was synthesized as THP-1 with B the Boc group, C the 2,6-dichlorobenzyl (Dcb) group, and the 4-hydroxymethylphenylacetic acid (PAM) linker. Tyr was incorporated prior to branching to provide a convenient chromophore for eventual concentration determination. Branching was achieved by synthesizing Fmoc-[Lys(Boc)]$_2$-Tyr(Dcb)-Gly-PAM (SEQ ID NO:8) resin and deprotecting the $N^\alpha$- and $N^\epsilon$-amino groups. Fmoc-Ahx was then incorporated onto all three amino termini to provide a flexible spacer. Following incorporation of Fmoc-Ahx, 0.12 g of peptide-resin was deprotected with piperidine and treated with TFMSA and the product precipitated by methyl tBu ether. ES-MS analysis of the product showed the desired branched peptide molecular ions [M+H]$^+$=831.5 Da (calculated 833.6 Da) and [M+K]$^+$=870.5 Da (calculated 871.6 Da). Coupling of Fmoc-amino acids and Fmoc-Gly-Pro-Hyp was achieved with HBTU and HOBt. Incorporation of Fmoc-Gly-Pro-Hyp required no double couplings using 4-fold excesses, with less than 0.5% D-Hyp per Fmoc-Gly-Pro-Hyp incorporated. Fmoc removal was by 2% DBU plus 2% piperidine (to scavenge dibenzofulvene) in DMF. 0.138 g of peptide-resin was cleaved with TFMSA and THP-1 purified by reversed-phase HPLC. Yield of THP-1 was 38.5 mg (32.9% of overall theoretical yield). The homogeneity of THP-1 was confirmed by analytical reversed-phase HPLC (FIG. 2) and SEC. THP-1 apparent molecular weight was 11.7 kDa (calculated 11,960 Da) by SEC. Edman degradation sequence analysis gave the desired sequence (Gly-Pro-Hyp)$_8$-Gly-Glu-Phe-Tyr-Phe-Asp-Leu-Arg-Leu-Lys-Gly-Asp-Lys (SEQ ID NO:1).

Figure 3:
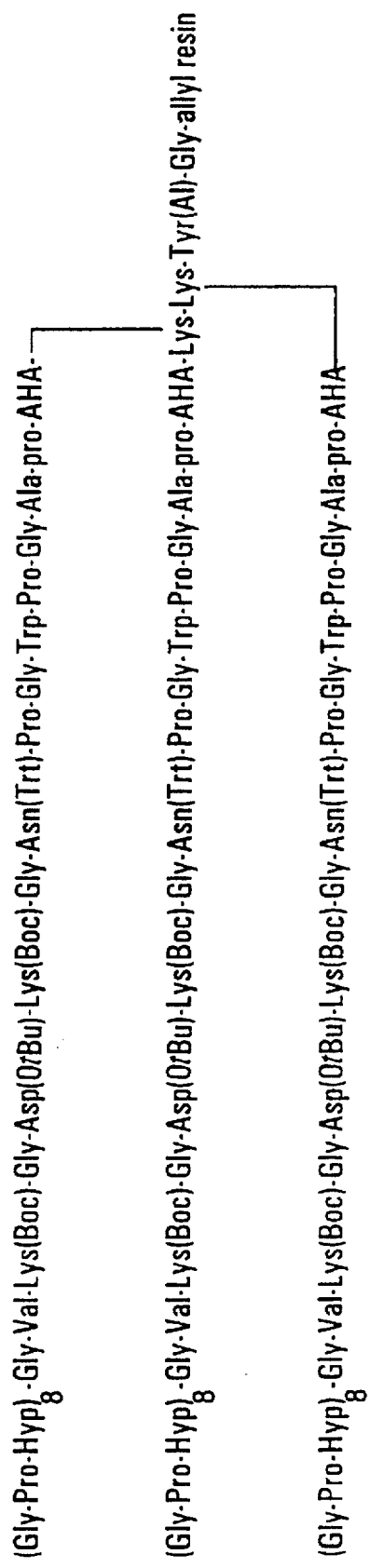
FIG. 3: Sequence of resin-bound, side-chain protected THP-2, which incorporates residues 1263–1277 from α1(IV) collagen. AHA=Ahx=6-aminohexanoic acid (SEQ ID NO:5), (SEQ ID NO:6), (SEQ ID NO:13).
Figure 4:
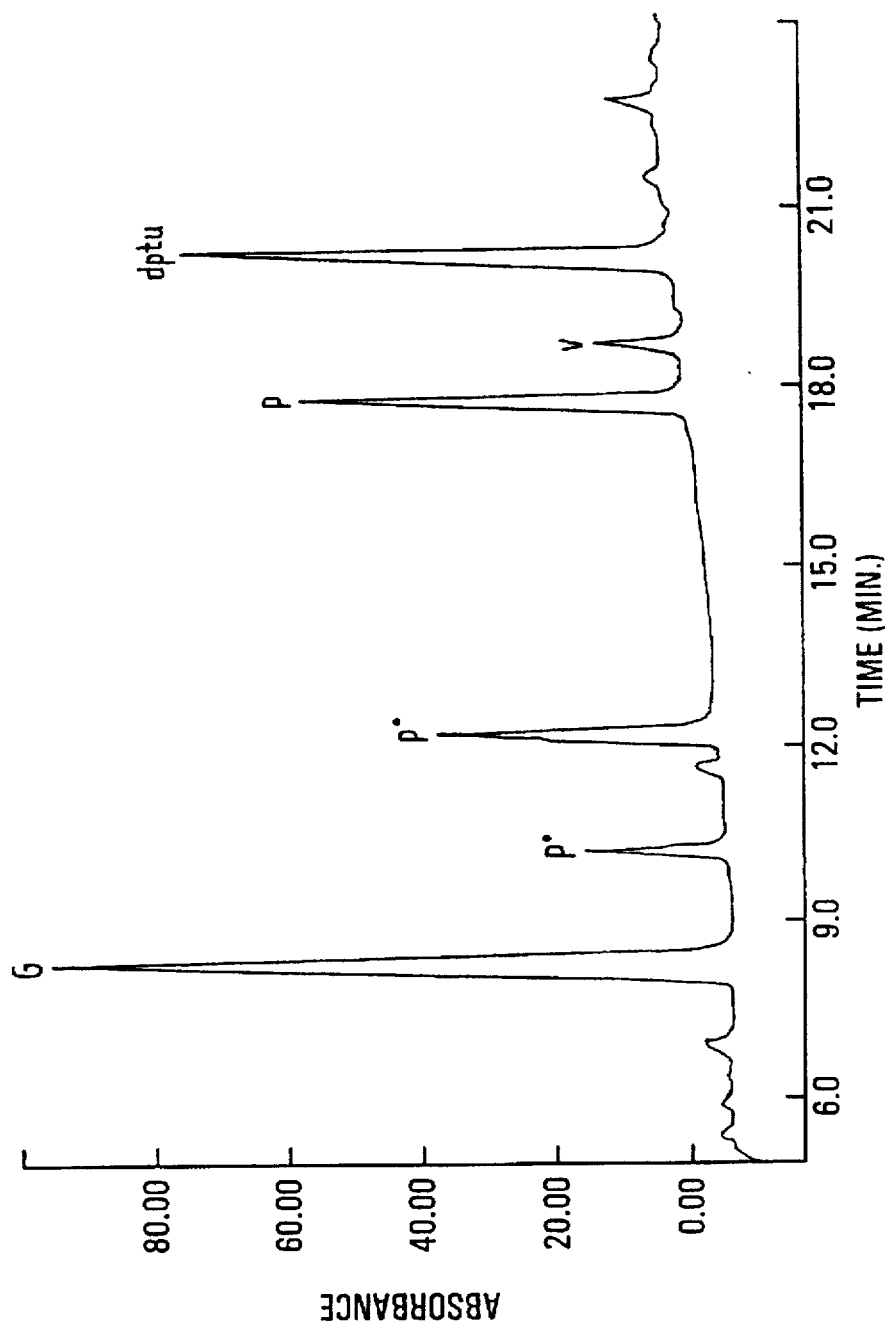
FIG. 4: Reversed-phase HPLC elution profile of PTH-amino acids in cycle 25 of solid-phase Edman degradation sequence analysis of resin-bound THP-2.
Figure 5:
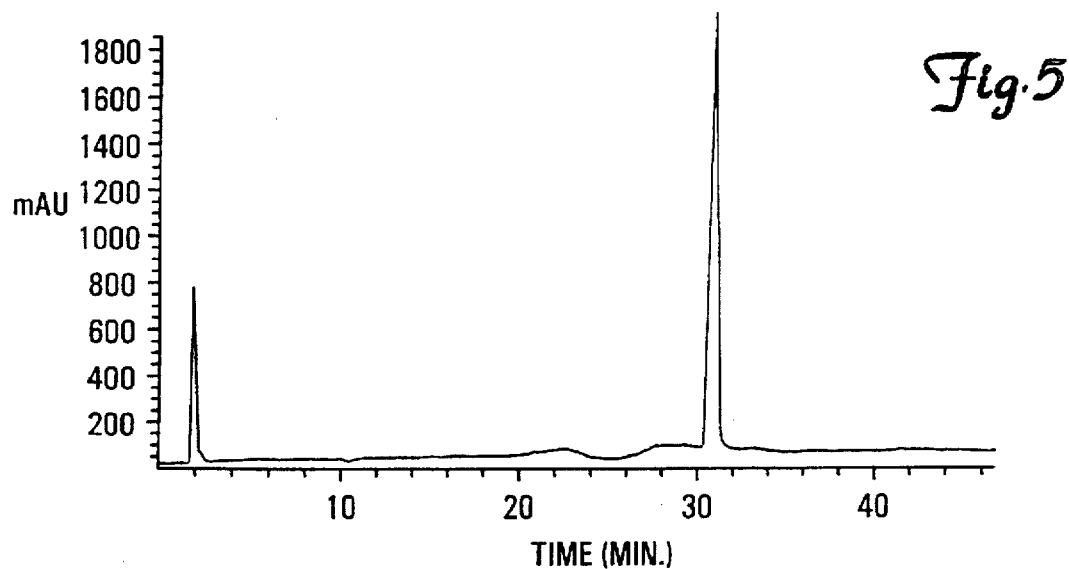
FIG. 5: Analytical reversed-phase HPLC elution profile of purified THP-2. Gradient was from 0–60% B in 60 min. Other conditions are given under Experimental Section.

THP-2, which incorporated the 1265–1277 sequence of α1(IV)collagen, was synthesized with a three-dimensional orthogonal protecting group strategy, where B was the Boc group, C the allyl group, and linker the allyl-based 4-trityloxy-Z-but-2-enyloxyacetic acid. Branching was achieved by synthesizing Fmoc-[Lys(Boc)]$_2$-Tyr(Al)-Gly-allyl (SEQ ID NO:8) resin and deprotecting the $N^\alpha$- and $N^\epsilon$-amino groups. The allyl linker permitted solid-phase sequence analysis of the synthetic of peptide-resin assembly at three stages: (1) prior to branching, (2) following incorporation of the specific collagen sequence, and (3) following incorporation of the Gly-Pro-Hyp triplets. Highly efficient syntheses occurred at each of these stages for THP-2 (see FIG. 3). For example, solid-phase sequence analysis of the assembled THP-2-resin showed a cumulative total of 3% preview (FIG. 4). THP-2 was side-chain deprotected with TFA while still resin-bound, and cleaved with $(Ph_3P)_4Pd$. Efficiency of cleavage by $(Ph_3P)_4Pd$ was 85.2%. The $(Ph_3P)_4Pd$-THP-2 complex was dissolved in 0.5N HCl, extracted with diethyl ether and DCM, chromatographed on a G-25 column, and purified by reversed-phase HPLC. Yield of THP-2 was 6.7 mg (4.7% of theoretical). The homogeneity and composition of THP-2 was confirmed by sequence and amino acid analyses, scanning UV spectroscopy, analytical reversed-phase HPLC (FIG. 5), and SEC. THP-2 apparent molecular weight was 11.6 Da (calculated 11,205 Da) by SEC at 4° C.

Allyl-based side-chain protection and a TFA-labile linker was used for the three-dimensional orthogonal synthesis of THP-3 [B=allyloxycarbonyl (Aloc), C=tBu, and linker= HMP (SEQ ID NO:8) in FIG. 1]. Both Aloc groups of [Lys(Aloc)]$_2$-Tyr(tBu)-Gly-HMP resin were removed with (Ph$_3$P)$_4$Pd at >95% efficiency. Following incorporation of Fmoc-Ahx, 0.20 g of peptide-resin was deprotected with piperidine and treated with TFA and the product precipitated by methyl tBu ether. ES-MS analysis of the product showed the desired branched peptide molecular ion [M+H]$^+$=833.8 Da (calculated 833.6 Da). THP-3 was assembled as described for THP-1. 0.182 g of peptide-resin was cleaved with TFA and THP-3 purified by reversed-phase HPLC. Yield of THP-3 was 9.8 mg (13.5% of theoretical). The homogeneity of THP-3 was confirmed by analytical reversed-phase HPLC (FIG. 2) and SEC. THP-3 apparent molecular weight was 6.92 kDa (calculated 7,250 Da) by SEC. Edman degradation sequence analysis gave the desired sequence (Gly-Pro-Hyp)$_8$ (SEQ ID NO:9).

THP-4, which incorporated the 1265–1277 sequence of α1(IV) collagen, was synthesized by a pseudo-three-dimensional orthogonal strategy [B=1-(4,4-dimethyl-2,6-dioxocyclohex-1-ylidene)ethyl (Dde), C=tBu, and linker=2-methoxy-4-alkoxybenzyl alcohol (SASRIN™) in FIG. 1]. Both Dde groups of [Lys(Dde)]$_2$Tyr(tBu)-SASRIN™ resin were removed with hydrazine at >95% efficiency. Following incorporation of Fmoc-Ahx, 0.10 g of peptide-resin was deprotected with piperidine and treated with TFA and the product precipitated by methyl tBu ether. ES-MS analysis of the product showed the desired branched peptide molecular ion [M+H]$^+$=777.4 Da (calculated 777.5 Da). THP-4 was assembled as described for THP-1. 0.094 g of peptide-resin was cleaved with TFA and THP-4 purified by reversed-phase HPLC. Yield of THP-4 was 10.2 mg (13.6% of theoretical). The homogeneity of THP-4 was confirmed by analytical reversed-phase (FIG. 2) and hydrophobic interaction (FIG. 6) HPLC and SEC. THP-4 apparent molecular weight was 7.76 kDa (calculated 7,135 Da) by SEC. Edman degradation sequence analysis gave the desired sequence (Gly-Pro-Hyp) 3-Gly-Val-Lys-Gly-Asp-Lys-Gly-Asn-Pro-Gly-Trp-Pro-Gly-Ala-Pro (SEQ ID NO:3). LD-TOF-MS gave [M+5H]$^+$ =1428 Da (calculated=1428.0 Da) and [M+4H]$^+$=1788 Da (calculated=1784.8 Da).

III. Circular Dichroism Spectroscopy of THPs

Figure 7:
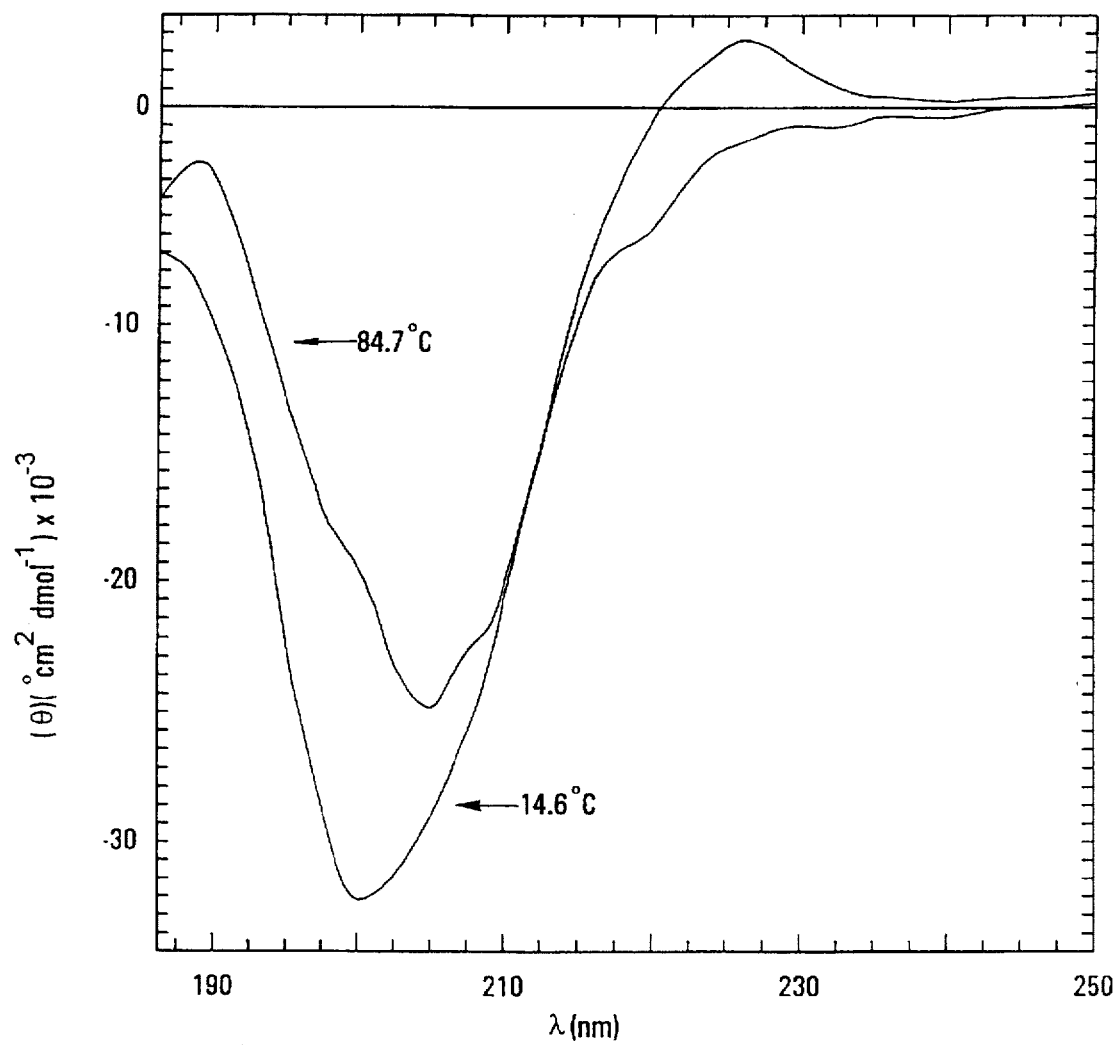
FIG. 7: CD spectra of THP-2 in 5% aqueous HOAc, pH 2.4, at 14.6° and 84.7° C. Conditions are given under Experimental Section.
Figure 10:
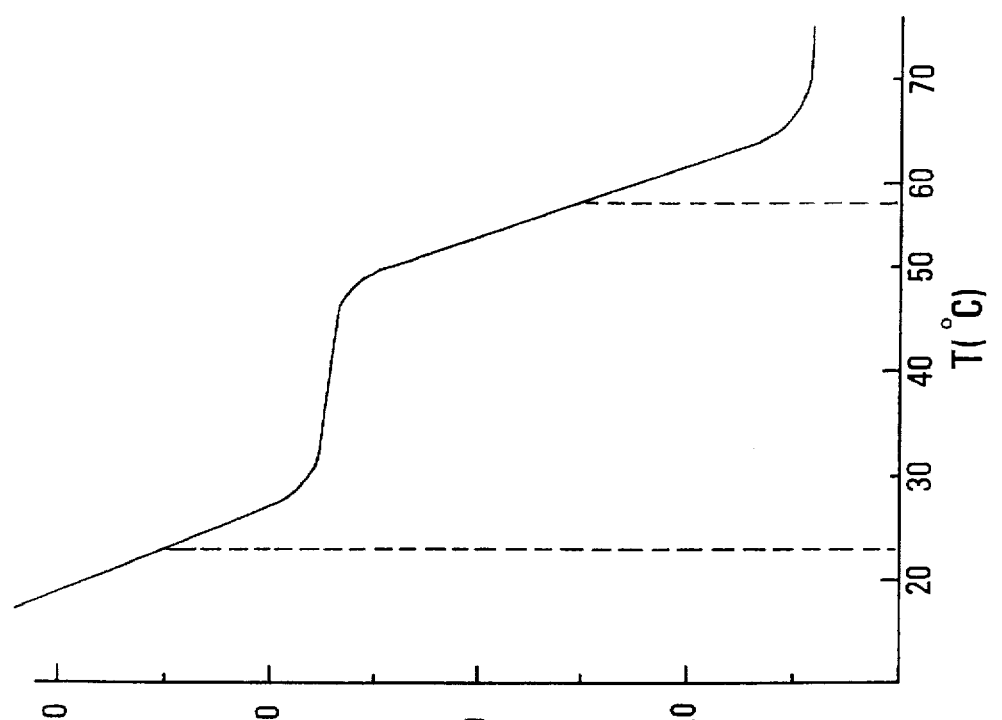
FIG. 10: Thermal transition curve for THP-2 in 5% aqueous HOAc, pH 2.4, λ=225 nm. Conditions are given under Experimental Section.
Figure 9:
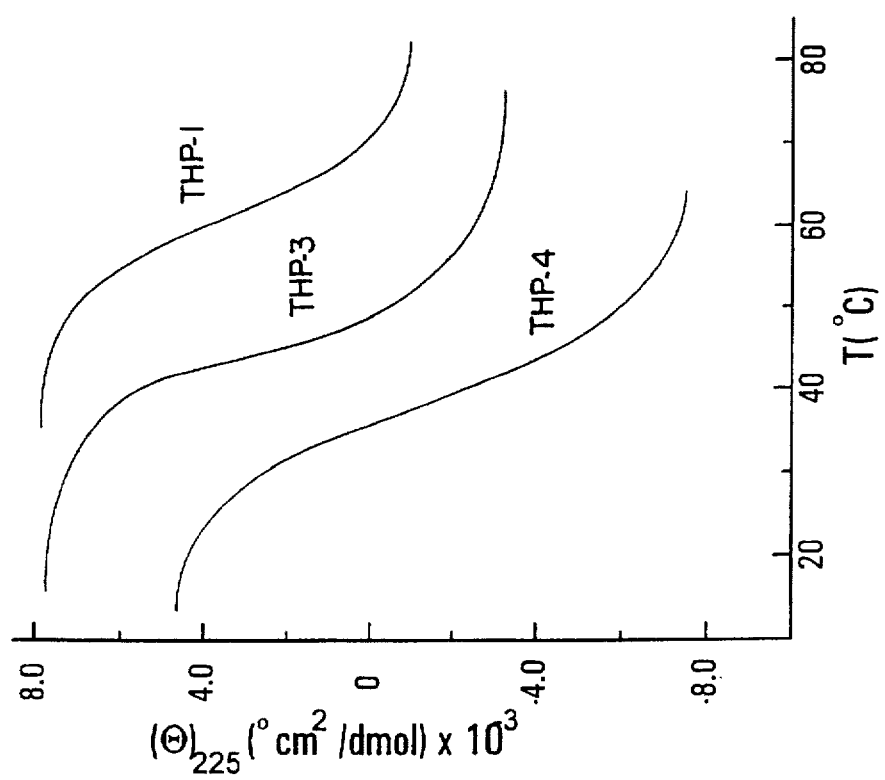
FIG. 9: Thermal transition curves for THP-1, THP-3, and THP-4 in 0.5–1% aqueous HOAc, pH 2.4, λ=225 nm. Conditions are given under Experimental Section.

CD spectra of THP-1, THP-2, THP-3, and THP-4 were characteristic of a coiled-coil triple-helix, with low temperature spectra exhibiting a large negative $[\theta]_{200}$ and a positive $[\theta]_{225}$ (FIGS. 7 and 8). As the temperature was increased, $[\theta]_{200}$ increased and $[\theta]_{225}$ decreased for all THPs. High temperature spectra were indicative of a melted triple-helix, as $[\theta]_{225}$ was negative. Melting of triple-helices was reversible. Single temperature-dependent triple-helical melts were seen for THP-1, THP-3, and THP-4, with $T_m$=53.0°, 42.5°, and 35.0° C., respectively (FIG. 9). Two temperature-dependent, reversible transitions were seen for THP-2 with midpoints at 23.5° and 58.5° C. (FIG. 10). SEC gave apparent THP-2 molecular weights of 11.6 kDa at 4° C. and 36.0 kDa at 35° C., indicating that the first transition was due to THP-2 aggregation. The second THP-2 transition was a triple-helical melt with $T_m$=58.5° C.

IV. Melanoma Cell Activities of THP-2

Figure 11:
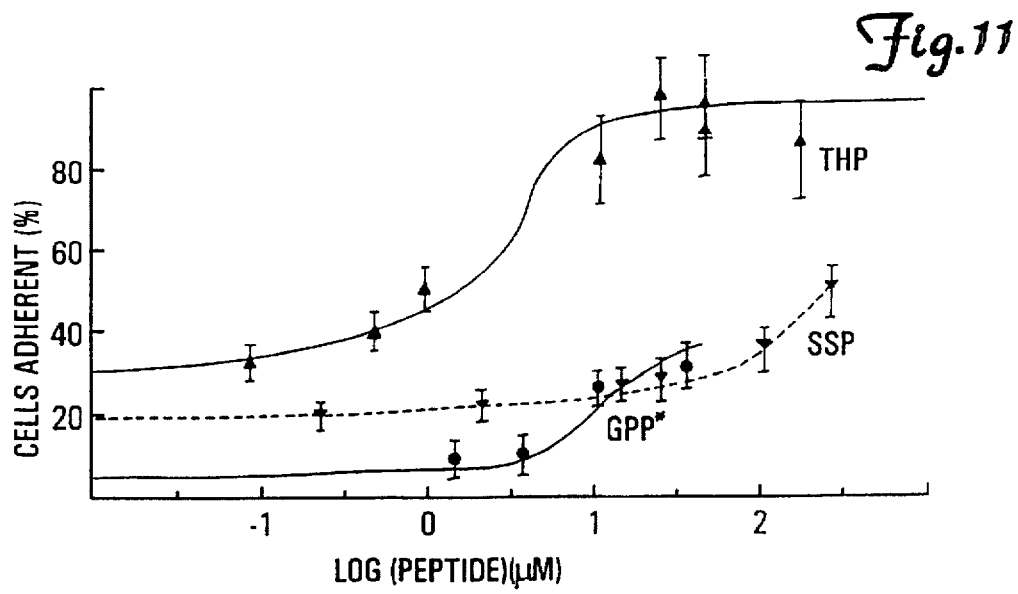
FIG. 11: Adhesion of melanoma cells as a function of THP-2, SSP, or THP-3 (GPP*) concentration. Cells were allowed to adhere to peptide-coated Immulon plates for 1 h at 37° C.

Melanoma cell adhesion was compared for THP-2, a single-stranded peptide (SSP) incorporating residues 1263–1277 from the α1 chain of type IV collagen, and THP-3 (GPP*) over a coated peptide concentration range of 0.1–300 μM. For the SSP concentration, a molecular weight of 4797 Da was used, where one mole of SSP accounted for three peptide chains. This conversion allowed for one mole of THP-2, SSP, or GPP* to represent three potential peptide active sites. The coating efficiencies for the three peptides were comparable, ensuring that cell adhesion results would not be a reflection of differential peptide adsorption to the plates. Half maximal melanoma cell adhesion occurred at [THP-2]=1.12 μM, [SSP]=170 μM, and [GPP*]>100 μM (FIG. 11). Thus, triple-helical conformation in combination with the α1(IV) 1263–1277 sequence resulted in a 100-fold increase in melanoma cell adhesion activity compared with the α1(IV) 1263–1277 sequence alone. This result is the first direct demonstration of the significance of triple-helicity for cell adhesion to a specific collagen sequence. Melanoma cell spreading was compared for THP-2, SSP, and GPP* at [THP-2]=0.9 μM, [SSP]=2.1 μM, and [GPP*]=1.4 μM. Cell spreading was more extensive on the THP-2 then on either the SSP or GPP*. For example, cell areas averaged 0.048, 0.012, and 0.017 mm$^2$/μM peptide in response to THP-2, SSP, and GPP*, respectively. As in the case of melanoma cell adhesion, cell spreading was most efficient when triple-helicity was combined with the α1(IV) 1263–1277 sequence.

Discussion and Implications of Results

A branching protocol was developed for solid-phase synthesis of triple-helical peptides to ensure alignment of the three peptide strands (FIG. 1). The branching protocol developed by Heidemann and coworkers for liquid-phase synthesis [W. Roth et al., Makromol. Chem. 180, 905 (1979) and H.-P. Germann et al., Biopolymers 27, 157 (1988)] used nitrophenylsulfenyl or Boc as the N$^\alpha$-amino protecting group, which was removed by moderate acidolysis, benzyloxycarbonyl (Cbz) as the Lys N$^\epsilon$-amino protecting group, which was removed by strong acidolysis, and 4-(2-chloropropionyl)phenylacetic acid as the linker, allowing for peptide-support cleavage by photolysis or saponification. The solid-phase synthesis of THP-1 relied upon acidic and basic deprotection mechanisms, as the N$^\alpha$-amino group was protected by the Fmoc group (A), which is base-labile and stable to acidolysis, the N$^\epsilon$-amino group was protected by the Boc group (B), which is acid-labile and stable to base, and the C$^\alpha$-carboxyl group was attached to the resin by PAM (linker), which is labile to strong acid and mild acid- and base-stable. Dcb side-chain protection, which is strong acid labile, was used for Tyr (C). To induce triple-helicity, Gly-Pro-Hyp triplets were incorporated following the specific collagen sequences. Coupling of Fmoc-amino acids and Fmoc-Gly-Pro-Hyp was achieved with HBTU, which allows for rapid kinetics and the use of optimal peptide-resin solvation conditions. Syntheses involving Hyp required special considerations. HBTU-mediated couplings have been shown to result in esterification of Fmoc-amino acids [C. G. Fields et al., Peptide Res. 6, 39 (1993)], suggesting a possible need for 4-hydroxyl side-chain protection of Hyp. The level of esterification with HBTU is ~4% for imino acids when a 10-fold excess of imino acid and HBTU is used in comparison to reactive sites on the resin [C. G. Fields et al., Peptide Res. 6, 39 (1993)]. For our syntheses, Hyp could only be esterified by an imino acid (i.e., Fmoc-Gly-Pro-Hyp). By using only a 4-fold excess of activated amino acid to reactive sites the level of imino acid esterification was anticipated to be much lower than the 4% reported previously, and thus Hyp was not side-chain protected. We found incorporation of Fmoc-Gly-Pro-Hyp to proceed smoothly using 4-fold excesses, with no indication of side-chain esterification and no double-couplings needed.

DBU was used for removing the Fmoc group. As chain length increases, the rate of Fmoc removal by piperidine can decrease, particularly in regions where interchain association due to secondary structure formation occurs. DBU has been shown to have several advantages over piperidine, in that the Fmoc group is removed efficiently even in "difficult" sequences [J. D. Wade et al., Peptide Res. 4, 194 (1991)]. The rapid kinetics of Fmoc removal by DBU allows for lower DBU concentrations (2%) than piperidine (20%) in DMF or NMP. Fmoc removal solutions should be of the highest possible DMF or NMP concentrations to most effectively solvate the peptide-resin. Our DBU solutions were 96% DMF or NMP, with 2% piperidine added to inhibit dibenzofulvene reattachment to the N-terminus of the peptide-resin.

Although successful, the methodology used for THP-1 does not allow for the incorporation of glycosylated residues, as O-glycosidic bonds are not stable to repetitive moderate acid deprotection and strong acid cleavage conditions. Glycosylated Hyl residues are located within both type IV collagen cell adhesion sequences and may serve as recognition sites for cell surface galactosyltransferase. A methodology compatable with the incorporation of glycosylated residues was achieved by using a mild three-dimensional orthogonal protecting group strategy. The $N^\alpha$-amino group was protected by the Fmoc group (A), which is base-labile and stable to acidolysis and palladium-catalyzed nucleophilic transfer. The $N^\epsilon$-amino group was protected by the Boc group (B), which is acid-labile and stable to base and palladium-catalyzed nucleophilic transfer. The $C^\alpha$-carboxyl group was attached to the resin by 4-trityloxy-Z-but-2-enyloxyacetic acid (linker), which is labile to palladium-catalyzed nucleophilic transfer and acid- and base-stable. We also used allyl-based side-chain protection for Tyr (C), which is labile to palladium-catalyzed nucleophilic transfer and acid- and base-stable. THP-2 assembly and cleavage were highly efficient using this methodology. However, removal of the $(Ph_3P)_4Pd$ from THP-2 was extremely difficult. The low yield of THP-2 (4.7%) was due to the extensive purification required to remove THP-2-complexed $(Ph_3P)_4Pd$.

An alternative three-dimensional methodology was used for THP-3, where the $N^\alpha$-amino group was protected by the Fmoc group (A), the $N^\epsilon$-amino group was protected by the Aloc group (B), and the $C^\alpha$-carboxyl group was attached to the resin by HMP (linker), which is acid-labile and stable to base and palladium-catalyzed nucleophilic transfer. Tyr was protected by the tBu group (C). Assembly was highly efficient using this methodology and thus only a one-step purification procedure was required. The 13.5% yield of THP-3 was a considerable improvement over the yield of THP-2. A pseudo-three-dimensional methodology was used for THP-4, where the $N^\alpha$-amino group was protected by the Fmoc group (A), the $N^\epsilon$-amino group was protected by the Dde group (B), which is labile to hydrazine, acid-stable, and moderately base-stable [B. W. Bycroft et al., J. Chem. Soc. Chem. Commun., 778 (1993)], and the $C^\alpha$-carboxyl group was attached to the resin by SASRIN™ (linker), which is acid-labile and stable to base and hydrazine. Since Lys(Dde) is not completely stable to piperidine, this strategy is not truly three dimensionally orthogonal. Tyr was protected by the tBu group (C). As for THP-3, assembly of THP-4 was highly efficient and a one-step purification procedure was utilized. The 13.6% yield of THP-4 was comparable to the yield of THP-3. For both THP-3 and THP-4, the lower yields compared with THP-1 were due to inefficient (~20–25%) release of the assembled peptides from the resin by TFA.

Figure 6:
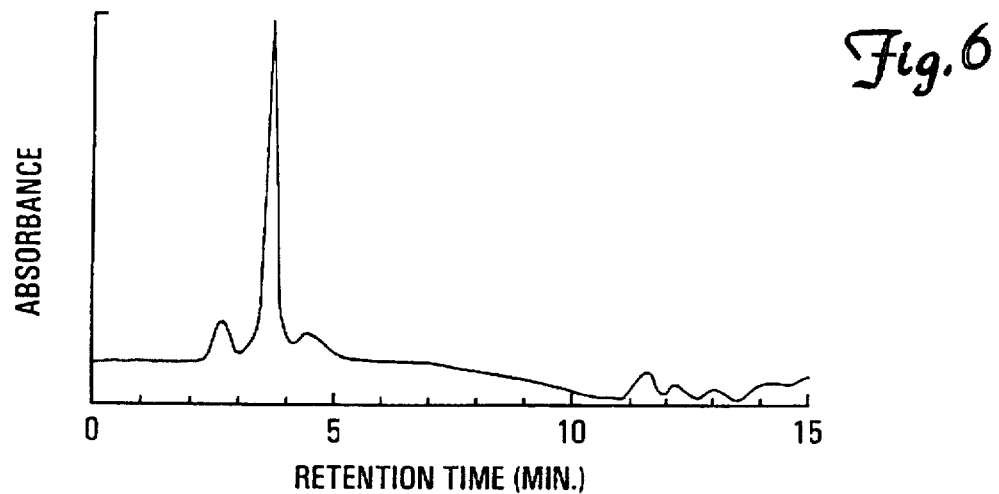
FIG. 6: Analytical hydrophobic interaction HPLC elution profile of purified THP-4. Gradient was from 0–100% B in 15 min, where A was 1.7M ammonium phosphate plus 0.1M sodium phosphate and B was 0.1M sodium phosphate. Other conditions are given under Experimental Section. The product eluting at 2.5 min is HOAc.

All THPs were homogeneous and correct compositionally by Edman degradation sequence analysis, analytical HPLC, and SEC. Reversed-phase C-18 HPLC of THP-4 (FIG. 2) gave a single peak at 26 min with broadening near the baseline. Analysis of THP-4 by reversed-phase C-4 HPLC gave a single, broader peak with less baseline broadening (data not shown), while hydrophobic interaction HPLC gave a homogeneous product (FIG. 6). No substantial heterogeneity of THP-4 was found by sequence analysis or SEC. Apparent THP molecular weights determined by SEC were within +8% of calculated values. Branch assembly was documented successfully by ES-MS. LD-TOF-MS gave molecular ions corresponding to desired THP-4. CD spectra of THP-1, THP-2, THP-3, and THP-4 were highly characteristic of triple-helical collagen and other collagen-model polypeptides. To determine THP triple-helix melting temperatures (triple-helix⇌coil transition), [θ] was monitored at 225 nm. THP-1, THP-2, THP-3, and THP-4 had $T_m$=53.0°, 58.5°, 42.5°, and 35.0° C., respectively. Large differences in THP $T_m$ were found for differences in chain length only (i.e., THP-2 versus THP-3), not sequence (i.e., THP-1 versus THP-2). When $T_m$ was normalized for chain length ($T_m$/triplet), resulting values for our and other THP triple-helical melts could be correlated to Hyp content. Although THP-1 contains an interruption in the Gly-X-Y repeat, it has a similar $T_m$/triplet value as THP-2, which has no Gly-X-Y interruptions. The similar $T_m$ values for THP-1 and THP-2 are probably due to (i) the large number (8) of Gly-Pro-Hyp repeats at the THP N-terminus, providing a cooperative "cluster" which stabilizes the triple-helix, and (ii) the branched Lys—Lys structure, which aligns and entropically stabilizes the C-terminus of the THP.

THP-2 had a low temperature transition with a midpoint at 23.5° C., which was shown by SEC to be the aggregation of THP-2 molecules. Aggregation induced by increasing temperature from 15°–30° C. is indicative of a hydrophobically driven process. Hydrophobic interactions have been described as the driving force for D-periodic symmetric collagen fibers, where aggregation occurs as an antiparallel association of individual triple-helices [B. B. Doyle et al., J. Mol. Biol. 91, 79 (1975)]. Aggregation of (Pro-Pro-Gly)$_{10}$ (SEQ ID NO:11) and (Pro-Pro-Gly)$_{20}$ (SEQ ID NO:12) triple-helices is an antiparallel association [B. R. Olsen et al., J. Mol. Biol. 57, 589 (1971)], and thus a hydrophobically driven ordered aggregation of triple-helical peptides is possible.

The combined melanoma cell THP-2 adhesion and spreading activities supports the concept that tumor cell adhesion and spreading on type IV collagen involves multiple, distinct domains, as at least two domains within type IV collagen in triple-helical conformation are tumor cell adhesion sites [M. K. Chelberg et al., Cancer Res. 49, 4796 (1989) and P. Vandenberg et al., J. Cell Biol. 113, 1475 (1991)]. In addition, the enhancement of cellular activities due to triple-helicity confirms the α1(IV) 1263–1277 sequence as a specific melanoma cell adhesion and spreading site, as this sequence in its native conformation has greater activity than the isolated sequence, and implies that basement membrane type IV collagen is a site for tumor cell invasion based on collagen primary, secondary, and tertiary structures. The enhancement of cellular activities by triple-helicity may allow for the development of THPs as anti-metastatic or anti-platelet aggregatory therapeutics.

We have demonstrated that aligned, triple-helical collagen-model peptides can be synthesized without repetitive or strong acidolysis. In general, strong acidolysis cleavage conditions are less desirable than moderate acidolysis. More specifically, our mild orthogonal methodology will allow efficient incorporation of glycosylated residues as well as single site $^2$H-, $^{15}$N-, and $^{13}$C-labeled residues for study of triple-helical conformation by NMR. The use of a C-terminal nucleation site allows for the synthesis and NMR structural studies of varying Gly-X-Y sequences with a minimum of Gly-Pro-Hyp triplets, and thus could overcome the problem of overlapping resonances due to the presence of primarily one type of repeating triplet [B. Brodsky et al., Biopolymers 32, 447 (1992)]. In addition to the orthogonal strategies utilized here, other combinations of protecting groups A, B, C, and linker (FIG. 1) can be utilized for the synthesis of collagen-model triple-helical peptides under mild conditions. These include $N^\alpha$- or $N^\epsilon$-amino protecting groups (A or B) labile to base (Fmoc or 2-[4-(methylsulfonyl)phenylsulfonyl]-ethoxycarbonyl (Mpc) [W. J. G. Schielen et al., Int. J. Peptide Protein Res. 37, 341 (1991)]), thiolysis (dithiasuccinoyl (Dts) [G. Barany et al., J. Am Chem. Soc. 99, 7363 (1977)] or 3-nitro-2-pyridinesulfenyl (Npys) [R. Matsueda et al., Int. J. Peptide Protein Res. 16, 392 (1980)]), photolysis (6-nitroveratryloxycarbonyl (Nvoc) [A. Patchornik et al., J. Am. Chem. Soc. 92, 6333 (1970)]); palladium-catalyzed nucleophilic transfer (Aloc), or hydrazine (Dde), $N^\epsilon$-amino protecting groups (B) labile to acid (Boc, 2-(4-biphenyl)propyl[2]oxycarbonyl (Bpoc) [S. S. Wang et al., Int. J. Peptide Protein Res. 1, 235 (1969)], 2-(3,5-dimethoxyphenyl)propyl[2]oxy-carbonyl (Ddz) [C. Voss et al., Hoppe-Seyler's Z. Physiol. Chem. 362, 717 (1981)], 4-methoxybenzyloxycarbonyl (Moz) [S. S. Wang et al., Int. J. Peptide Protein Res. 30, 662 (1987)], 1-(1-adamantyl)-1-methylethoxycarbonyl (Adpoc) [J. Shao et al., Tetrahedron Lett. 22, 345 (1991)], or triphenylmethyl (Trt) [K. Barlos et al., Liebigs Ann. Chem., 1025 (1987)]), and linkers labile to acid [HMP, 3-methoxy-4-hydroxymethylphenoxy, SASRIN™, 2-chlorotrityl chloride, 5-(4-hydroxymethyl-3, 5-dimethoxyphenoxy) (HAL), etc.], palladium-catalyzed nucleophilic transfer [4-hydroxy-Z-but-2-enyloxyacetyl (allyl) or hydroxycrotonyl-aminomethyl (Hycram)], fluoride ion ((3 or 4)-[[[(4-hydroxymethyl)phenoxy-t-butyl-phenyl]silyl]phenyl]pentanedioic acid, monoamide [D. G. Mullen et al., J. Org. Chem. 53, 5240 (1988)]), or photolysis (2-bromopropionyl [α-methylphenacyl ester] linker [S. S. Wang, J. Org. Chem. 41, 3258 (1976)]) [G. B. Fields et al., in *Synthetic Peptides: A User's Guide* (Grant, G. A., Ed.), pp. 77–183, W. H. Freeman & Co., New York (1992)]. Finally, by utilizing further dimensions of orthogonality, heterotrimeric triple-helical peptides can be synthesized.

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

---

What is claimed is:

1. A supported polypeptide of the formula:

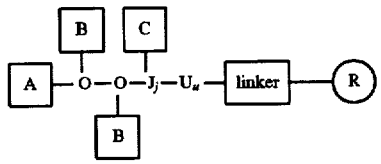

wherein:
- (a) A is an $N^{\alpha}$-amino protecting group capable of being removed under non-acidic conditions;
- (b) B is a side-chain amino protecting group capable of being removed under non-strong acidic conditions;
- (c) O is an amino acid having a single side-chain amino group;
- (d) J is an amino acid capable of acting as a chromophore;
- (e) C is a protecting group capable of withstanding the conditions in which A and B are removed;
- (f) U is an amino acid;
- (g) u=0 or 1;
- (h) j≧1;
- (i) the linker is capable of being labilized using a non-strong acid mechanism; and
- (j) R is a support material.

2. The supported polypeptide of claim 1 wherein A is Fmoc.

3. The supported polypeptide of claim 1 wherein C is capable of being removed under the same conditions as the linker.

4. The supported polypeptide of claim 3 wherein C is Dcb, allyl, or tBu.

5. The supported polypeptide of claim 1 wherein O is Lys.

6. The supported polypeptide of claim 1 wherein J is Tyr.

7. The supported polypeptide of claim 1 wherein U is Gly.

8. The supported polypeptide of claim 1 wherein the linker is allyl, HMP, or SASRIN™ (3-methoxy-4-hydroxymethylphenoxy).

9. The supported polypeptide of claim 1 wherein the support material is an organic polymeric material.

10. The supported polypolypeptide of claim 9 wherein the organic polymeric material comprises crosslinked polystyrene.

11. The supported polypeptide of claim 10 wherein the organic polymeric material further comprises polyethylene glycol.

* * * * *

UNITED STATES PATENT AND TRADEMARK OFFICE
CERTIFICATE OF CORRECTION

PATENT NO. : 5,726,243
DATED : March 10, 1998
INVENTOR(S) : Gregg B. Fields

It is certified that error appears in the above-identified patent and that said Letters Patent is hereby corrected as shown below:

Col. 2, line 32, delete "contritions" and insert --conditions--;

Col. 9, line 60, delete "to 4).5 mL" and insert --to ~0.5 mL--;

Col. 11, line 12, delete "desalter" and insert --desalted--;

Col. 13, lines 39-40, delete "(Gly-Pro-Hyp)3" and insert --(Gly-Pro-Hyp)$_3$--;

Col. 16, line 13, delete "+8%" and insert --±8%--; and

Col. 18, line 6, delete "Lett. 22, 345" and insert --Lett. 32, 345--.

Signed and Sealed this

Thirteenth Day of July, 1999

Attest:

*Attesting Officer*

Q. TODD DICKINSON

*Acting Commissioner of Patents and Trademarks*